(12) United States Patent
Li et al.

(10) Patent No.: US 12,318,282 B2
(45) Date of Patent: Jun. 3, 2025

(54) TRANSAPICAL IMPLANTABLE MITRAL VALVE DEVICE

(71) Applicant: SINO MEDICAL SCIENCES TECHNOLOGY INC., Tianjin (CN)

(72) Inventors: Zhonghua Li, Irvine, CA (US); Tianzhu Li, Tianjin (CN); Jianxiang Ma, Tianjin (CN); Jinhong Zhao, Tianjin (CN); Lei Meng, Tianjin (CN)

(73) Assignee: SINO MEDICAL SCIENCES TECHNOLOGY INC., Tianjin (CN)

( * ) Notice: Subject to any disclaimer, the term of this patent is extended or adjusted under 35 U.S.C. 154(b) by 831 days.

(21) Appl. No.: 17/049,636

(22) PCT Filed: Dec. 6, 2018

(86) PCT No.: PCT/CN2018/119502
§ 371 (c)(1),
(2) Date: Oct. 22, 2020

(87) PCT Pub. No.: WO2019/205644
PCT Pub. Date: Oct. 31, 2019

(65) Prior Publication Data
US 2021/0361418 A1    Nov. 25, 2021

(30) Foreign Application Priority Data

Apr. 26, 2018    (CN) .......................... 201810386284.0

(51) Int. Cl.
*A61F 2/24*     (2006.01)
*A61L 27/16*    (2006.01)
*A61L 27/36*    (2006.01)

(52) U.S. Cl.
CPC ............ *A61F 2/2418* (2013.01); *A61L 27/16* (2013.01); *A61L 27/3625* (2013.01);
(Continued)

(58) Field of Classification Search
CPC ............ A61F 2/2418; A61F 2230/0013; A61F 2310/00389; A61F 2210/0014;
(Continued)

(56) References Cited

U.S. PATENT DOCUMENTS

2010/0262231 A1* 10/2010 Tuval .................... A61F 2/2409
                                                    623/2.4
2013/0304200 A1* 11/2013 McLean ................ A61F 2/2412
                                                    623/2.18
(Continued)

FOREIGN PATENT DOCUMENTS

CN         104188737 A      12/2014
CN         104771247 A       7/2015
(Continued)

OTHER PUBLICATIONS

International Search Report issued Feb. 27, 2019 in the parent application PCT/CN2018/119502 (4 pages).

*Primary Examiner* — Suzette J Gherbi
(74) *Attorney, Agent, or Firm* — Polsinelli PC

(57) ABSTRACT

The present invention provides a transapical implantable mitral valve device, which includes an outer valve stent comprising an outer valve stent body that is composed of a plurality of first structure units arranged in the circumferential direction and an anchoring unit that is disposed on the outer valve stent body for anchoring the mitral valve device in a human body, at least one of an inner surface and an outer surface of the outer valve stent body being covered with an outer skirt; an inner valve stent disposed inside the outer valve stent and interconnected with the outer valve stent, a cavity being formed between the outer valve stent and the inner valve stent; and a valve leaflet structure disposed in the inner valve stent to form a prosthetic valve.

19 Claims, 23 Drawing Sheets

(52) U.S. Cl.
CPC ............... *A61F 2210/0014* (2013.01); *A61F 2220/0075* (2013.01); *A61F 2230/0013* (2013.01); *A61F 2250/006* (2013.01)

(58) Field of Classification Search
CPC ........ A61F 2220/0075; A61F 2250/006; A61F 2220/0008; A61F 2230/005; A61L 27/16; A61L 27/3625
See application file for complete search history.

(56) References Cited

U.S. PATENT DOCUMENTS

| | | | | |
|---|---|---|---|---|
| 2013/0310917 | A1* | 11/2013 | Richter | A61F 2/2433 623/1.12 |
| 2014/0194983 | A1* | 7/2014 | Kovalsky | A61F 2/2445 623/2.38 |
| 2014/0243396 | A1 | 8/2014 | Garde et al. | |
| 2015/0142100 | A1* | 5/2015 | Morriss | A61F 2/2436 623/2.4 |
| 2015/0173897 | A1* | 6/2015 | Raanani | A61F 2/2418 623/2.11 |
| 2015/0351904 | A1* | 12/2015 | Cooper | A61F 2/2418 623/2.1 |
| 2016/0331531 | A1 | 11/2016 | Quadri et al. | |
| 2017/0056166 | A1* | 3/2017 | Ratz | A61F 2/2418 |
| 2017/0095328 | A1 | 4/2017 | Cooper et al. | |
| 2017/0100236 | A1* | 4/2017 | Robertson | A61F 2/2403 |
| 2017/0189177 | A1* | 7/2017 | Schweich, Jr. | A61F 2/2436 |
| 2018/0014930 | A1* | 1/2018 | Hariton | A61F 2/243 |
| 2020/0054449 | A1* | 2/2020 | Min | A61F 2/2418 |

FOREIGN PATENT DOCUMENTS

| | | |
|---|---|---|
| CN | 105658108 A | 6/2016 |
| CN | 105658178 A | 6/2016 |
| CN | 105658179 A | 6/2016 |
| CN | 106175987 A | 12/2016 |
| CN | 107028685 A | 8/2017 |
| CN | 107205822 A | 9/2017 |
| CN | 107296667 A | 10/2017 |
| CN | 107787209 A | 3/2018 |
| CN | 107205818 A | 6/2018 |
| CN | 108135696 A | 6/2018 |
| CN | 108578016 A | 9/2018 |

\* cited by examiner

TRANSAPICAL IMPLANTABLE MITRAL VALVE DEVICE

This application is a National Phase of International Application No. PCT/CN2018/119502, filed on Dec. 6, 2018, which claims priority to Chinese Patent Application No. 201810386284.0, entitled "TRANSAPICAL IMPLANTABLE MITRAL VALVE DEVICE" filed on Apr. 26, 2018, the contents of which are expressly incorporated by reference herein in their entireties.

TECHNICAL FIELD

The present invention relates to field of medical instruments, in particular to a transapical implantable mitral valve device.

BACKGROUND

Mitral regurgitation (MR) refers to that the mitral valve is not closed tightly when the heart contracts, which makes the blood reversely flow from the left ventricle to the left atrium. There are many other causes of valve regurgitation, such as valve prolapse, valve sclerosis in the elderly, rheumatic valve disease in young and middle-aged people, infective inflammation of valve, cardiac enlargement and so on. This causes to prevent the left ventricle from filling during diastole.

According to the severity, the manifestations of mitral regurgitation vary greatly. Mild mitral regurgitation cannot appear clinical symptoms for a long time and has a good prognosis; severe mitral regurgitation can lead to pulmonary hypertension, atrial fibrillation, heart failure, shock and death. According to severity of the disease, mitral regurgitation can be divided into acute and chronic MR. Patients with acute severe mitral regurgitation have poor tolerance, which may cause severe pulmonary edema and shock, and have poor prognosis. For chronic severe MR, patients will appear symptoms within 6-10 years. The incidence rate of all-cause death, cardiac death and cardiovascular events for asymptomatic ones within 5 years are 22±3%, 14±3% and 33±3%, respectively. And the mortality rate of patients with severe heart failure is 34% per year. A number of studies have shown that mitral regurgitation is a powerful and independent predictor of prognosis in patients with heart failure, and the mortality rate of patients with moderate or severe mitral regurgitation is significantly higher than that of patients without or with mild mitral regurgitation.

There are about 20 million patients with mitral regurgitation currently in China. At present, the standard mitral valve operation in China is open sternotomy, which uses cardiopulmonary bypass to stop the heart and implants mechanical or biological prosthetic valve, wherein the artificial biological valve is a central blood flow type, which is close to the normal function of the prosthetic valve, has good hemodynamic performance, little damage to the blood components, low incidence of thromboembolism, and no need for lifelong anticoagulation after operation, and thus avoid bleeding complications caused by over dosage of anticoagulants. Although the biological prosthetic valve replacement technology is relatively mature, long-term durability has been clinically proven, but the operation is very difficult and the trauma is large. Most of patients are in a dilemma that they cannot be cured by taking medicines, while there is a high risk in the thoracotomy operation of mitral valve repair.

Recently, a transcatheter technique has been developed to introduce and implant artificial heart valves by utilizing soft catheters in a much less invasive manner than open heart surgery. In this technique, the prosthetic valve is installed on the end part of the soft catheter in a curled state and advances through the patient's blood vessels until the valve reaches the implanted position. The valve at the end of the catheter is then located at the defective native valve, and a valve stent is anchored at the native valve through balloon dilation or self-expansion.

Another known technique for implanting an artificial aortic valve is a transapical approach, which creates a small incision in chest wall of the patient, and the catheter moves through the apex (i.e., the bottom end) until the valve reaches the implanted position.

The unique anatomical structure of the mitral valve presents a great challenge to the transcatheter mitral valve replacement device. Firstly, the contour shape of mitral valve annulus is not symmetrical and uniform, but non-circular D shape or kidney like shape. This unpredictability makes it difficult to design a mitral valve replacement device that fits the contour shape of the mitral valve annulus completely. If the mitral valve replacement device and the native valve leaf and/or the valve annulus cannot fully fit, it may leave gaps in them, which will cause the blood to flow back to the left atrium through these gaps, forming a perivalvular leakage.

Secondly, the mitral valve annulus lacks radial support from surrounding tissue. Unlike the aortic valve, which is completely surrounded by fibrous elastic tissue, the mitral valve annulus can support and fix the prosthetic valve by providing its native structure characteristics; the mitral valve is bound to the outer wall only by muscle tissue. The inner wall of the mitral valve is bound by a thin vascular wall, which separates the mitral valve annulus from the internal part of the aortic outflow tract. Therefore, if a relatively large radial support force is applied to the mitral valve annulus, such as the support force provided by the dilated stent, it may lead to collapse of the internal part of the aortic outflow tract, with potentially fatal consequences.

In view of the difficulties associated with current methods, there is still a need for devices and methods that can be firmly positioned, effective and less invasive for the treatment of dysfunctional heart valves.

The above statement of background technology is only for convenience of deep understanding of technical solutions of the present invention (technical means used, technical problems solved, technical effects brought, etc.), and shall not be deemed as recognition or implication in any form that the information constitutes the prior art known to those skilled in the art.

SUMMARY OF THE PRESENT INVENTION

Based on the above purposes, the present invention provides a transapical implantable mitral valve device, which includes: an outer valve stent comprising an outer valve stent body that is composed of a plurality of first structure units arranged in a circumferential direction, and an anchoring unit that is disposed on the outer valve stent body for anchoring the mitral valve device within a human body; an inner surface and/or an outer surface of the outer valve stent body being covered with outer skirt; an inner valve stent disposed inside the outer valve stent and interconnected with the outer valve stent, a cavity being formed between the outer valve stent and the inner valve stent; and a valve leaflet structure disposed inside the inner valve stent to form a prosthetic valve.

In a specific embodiment, the inner valve stent includes an inner valve stent body composed of a plurality of second structure units arranged in the circumferential and axial directions.

In a specific embodiment, an inner surface and/or an outer surface of the inner valve stent are covered with inner skirt.

In an alternative embodiment, materials of the outer valve stent and the inner valve stent are selected from hyperelastic alloy and shape memory alloy materials.

In a specific embodiment, tail ends of a plurality of the second structure units at the left ventricular end of the mitral valve device extend and turn out to form a first connecting structure that is connected with the first structure units of the outer valve stent body so as to connect the outer valve stent with the inner valve stent, and a cavity is formed between the outer valve stent and the inner valve stent; optionally, an angle of turning out is 15 degrees to 165 degrees.

In a specific embodiment, the left ventricular end of the first structure units turns in to form a second connecting structure that is connected with the second structure units of the inner valve stent body so as to connect the outer valve stent with the inner valve stent, and a cavity is formed between the outer valve stent and the inner valve stent; optionally, an angle of turning in is 15 degrees to 165 degrees.

In a specific embodiment, tail ends of a plurality of the second structure units at the left ventricular end of the mitral valve device extend and turn out to form a first connecting structure, the left ventricular end of the first structure units turns in to form a second connecting structure that is connected with the first connecting structure so as to connect the outer valve stent with the inner valve stent, and a cavity is formed between the outer valve stent and the inner valve stent; optionally, both an angle of turning out and an angle of turning in are 15 degrees to 165 degrees.

In an alternative embodiment, an inside or outside of the first connecting structure and/or an inside or outside of the second connecting structure is provided with joint skirt.

In a specific embodiment, the first structure units are provided with a plurality of sets of holes, the left ventricular end of the second structure units, the structure unit joint of the second structure units and/or the left atrial end of the second structure units are provided with filamentous connecting structures, each filamentous connecting structure penetrates into each hole of a set of the holes and is fixed, so as to connect the outer valve stent with the inner valve stent, and a cavity is formed between the outer valve stent and the inner valve stent; optionally, an angle formed between the filamentous connecting structures and the axial direction of the mitral valve device is 15 degrees to 165 degrees.

In an alternative embodiment, the number of holes for each set of the holes is 2-5.

In a preferred embodiment, in case that the left ventricular end of the second structure units is provided with filamentous connecting structures, and the structure unit joint or the left atrial end of the second structure units is provided with filamentous connecting structures, the number of filamentous connecting structures at the structure unit joint or the left atrial end is less than the number of filamentous connecting structures at the left ventricular end.

In an alternative embodiment, the number of filamentous connecting structures at the left ventricular end is 6-15; the number of filamentous connecting structures at the structure unit joint or at the left atrial end is 2-5.

In a specific embodiment, the inner valve stent is an improved surgical biological prosthetic valve, which includes a frame, a valve leaflet structure arranged inside the frame, and an annular sealing ring arranged at the left atrial end of the frame, wherein the frame and the annular sealing ring are compressible.

In a specific embodiment, the improved surgical biological prosthetic valve after compression in the radial direction has a radius of less than 15 mm, so that the mitral valve device is loaded into the sheath.

In a specific embodiment, a plurality of filamentous connecting structures are arranged at periphery of the annular sealing ring, and a plurality of sets of holes are arranged on the outer valve stent, each filamentous connecting structure passes through a set of said holes and is fixed, so that the outer valve stent is connected with the inner valve stent, and a cavity is formed between the outer valve stent and the inner valve stent; optionally, the acute angle formed by the filamentous connecting structures and the axial direction of the mitral valve device is 15 degrees to 75 degrees.

In a specific embodiment, a clip structure is provided at the end of the first structure units of the outer valve stent near the left atrial, which is used to hold the annular sealing ring, so that the outer valve stent is connected with the inner valve stent, and a cavity is formed between the outer valve stent and the inner valve stent.

In a specific embodiment, the anchoring unit includes an U-shaped structure unit and an S-shaped structure unit, wherein the U-shaped structure unit is provided at the left atrial end of the outer valve stent body to locate the mitral valve device at the mitral valve annulus, and the S-shaped structure unit is provided at the left ventricular end of the outer valve stent body to fix with the mitral valve leaflet.

In a specific embodiment, terminal of the left atrial end of the U-shaped structure unit and terminal of the left ventricular end of the S-shaped structure unit are provided with pull rings; optionally, the shape of the pull rings is circular, rounded rectangle, preferably rounded rectangle.

In a specific embodiment, a vertical distance between the horizontal plane on which endpoint of the S-shaped structure unit near the left atrial end locates and the horizontal plane on which endpoint of the U-shaped structure unit near the left ventricular end locates is 0.5 mm to 4 mm.

In a specific embodiment, the S-shaped structure unit has a thickness on the radial direction of 0.5 mm to 4 mm.

In a specific embodiment, a plurality of the U-shaped structure units constitute a circular structure which has a large circle diameter of 55 mm to 65 mm.

In a specific embodiment, the first structure unit and/or the second structure unit are provided to be 6-15.

In a specific embodiment, the cavity formed between the outer valve stent and the inner valve stent has a thickness in the radial direction of not less than 1.5 mm.

In a specific embodiment, the outer skirt, the inner skirt and/or the joint skirt are arranged to seal the mitral valve device, leaving an opening only at the valve leaflet structure to pass through blood.

In an alternative embodiment, material of the valve leaflet structure is animal pericardium or polymer material, preferably, material of the valve leaflet structure is bovine pericardium, pig pericardium, polytetrafluoroethylene, fiber cloth or fiber membrane; material of the outer skirt is animal pericardium or polymer material, preferably, material of the outer skirt is bovine pericardium, pig pericardium, polytetrafluoroethylene, fiber cloth or fiber membrane; material of the inner skirt is animal pericardium or polymer material, preferably, material of the inner skirt is bovine pericardium, pig pericardium, polytetrafluoroethylene, fiber cloth or fiber membrane; material of the joint skirt is animal pericardium or polymer material, preferably, material of the joint skirt is bovine pericardium, pig pericardium, polytetrafluoroethylene, fiber cloth or fiber membrane.

It can be seen that the transapical delivery mitral valve device provided by the present invention is used to implant into the in-situ mitral valve with lesions caused by mitral valve stenosis or mitral valve regurgitation/insufficiency, which has the following advantages:

1. It can be accurately transported to and firmly anchored at the position of the diseased mitral valve;
2. It ensures that the biological valve prosthesis is not affected by irregular contour of the diseased mitral valve, and always keeps the ideal contour to ensure functions;
3. It can provide a platform for interventional therapy for the surgical-type mitral valve device.

DETAILED DESCRIPTION OF EMBODIMENTS

Hereinafter, the present invention will be further described in combination with the accompanying drawings.

It should be understood that the appended drawings are not drawn to scale, but merely to illustrate a properly simplified representation of various features of the basic principles of the present invention. The specific design features of the present invention disclosed herein including, for example, specific dimensions, directions, positions and shapes will be determined in part by the specific application and use environment.

The present invention concept of the present invention includes a plurality of specific embodiments, different embodiments have different technical or application emphases, different embodiments can be combined and matched to meet different application scenarios and solve different application requirements. Therefore, the following description of specific embodiments shall not be understood as a limitation of the technical solutions intended to be protected by the present invention.

Embodiment 1

Figure 1:
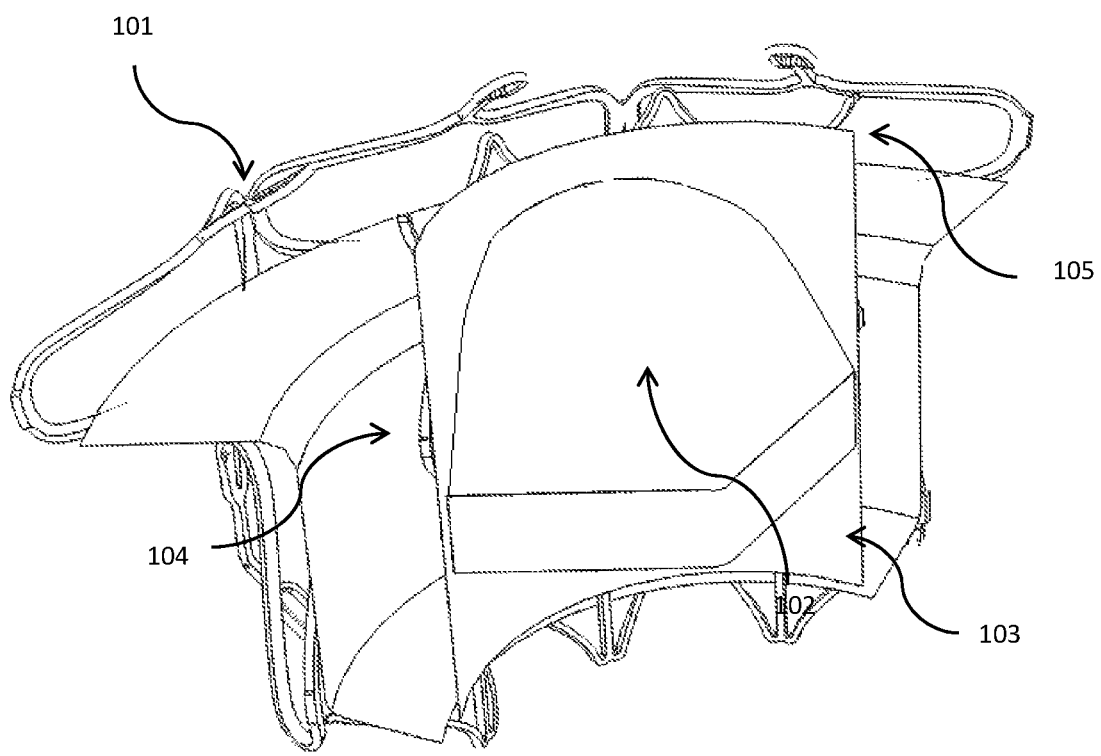
FIG. 1: a partial structure schematic view of a transapical implantable mitral valve device provided by a first embodiment of the present invention.

FIG. 1 is a partial structure schematic view of the transapical implantable mitral valve device provided in the first embodiment of the present invention. As shown in FIG. 1, in this embodiment, the transapical implantable mitral valve device includes an outer valve stent 101, an inner valve stent 103 and a valve leaflet structure 102, and an outer skirt 104 covering an inner surface and/or an outer surface of the outer valve stent 101 and an inner skirt 105 covering an inner surface and/or an outer surface of the inner valve stent 103.

Figure 2:
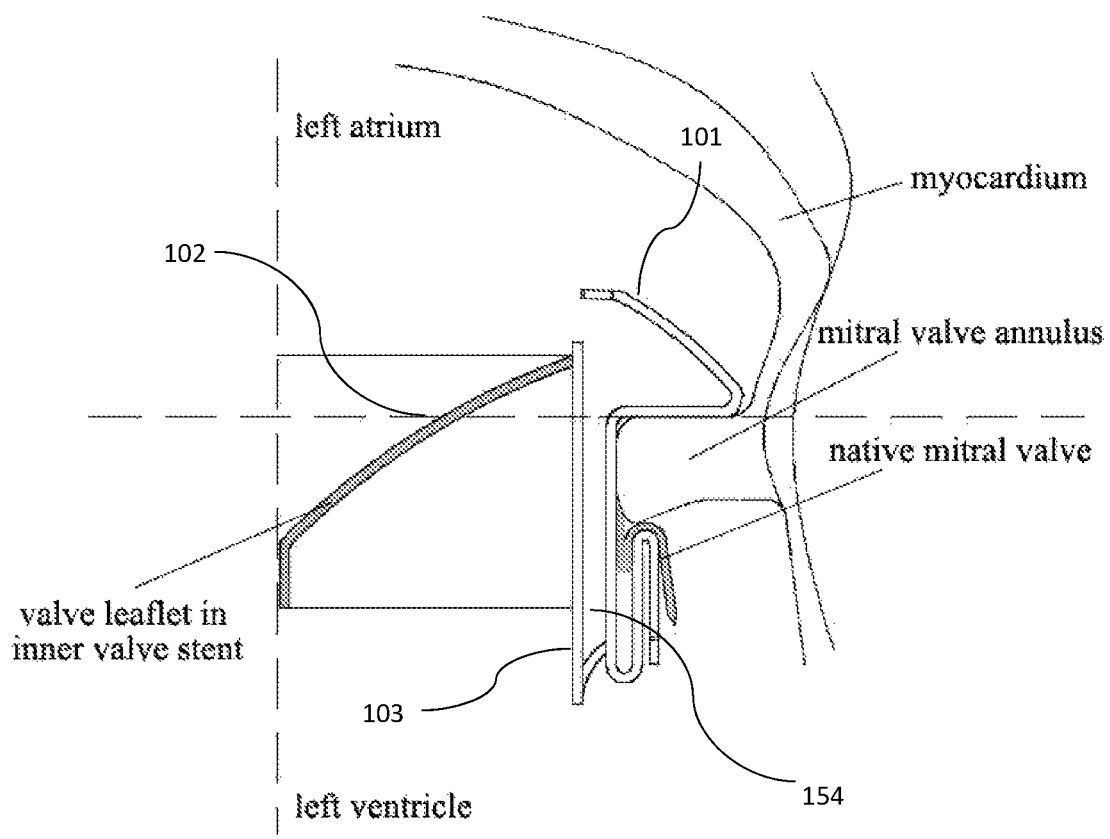
FIG. 2: a structure schematic view of the transapical implantable mitral valve device provided by the first embodiment of the present invention implanted into the human body.
Figure 3:
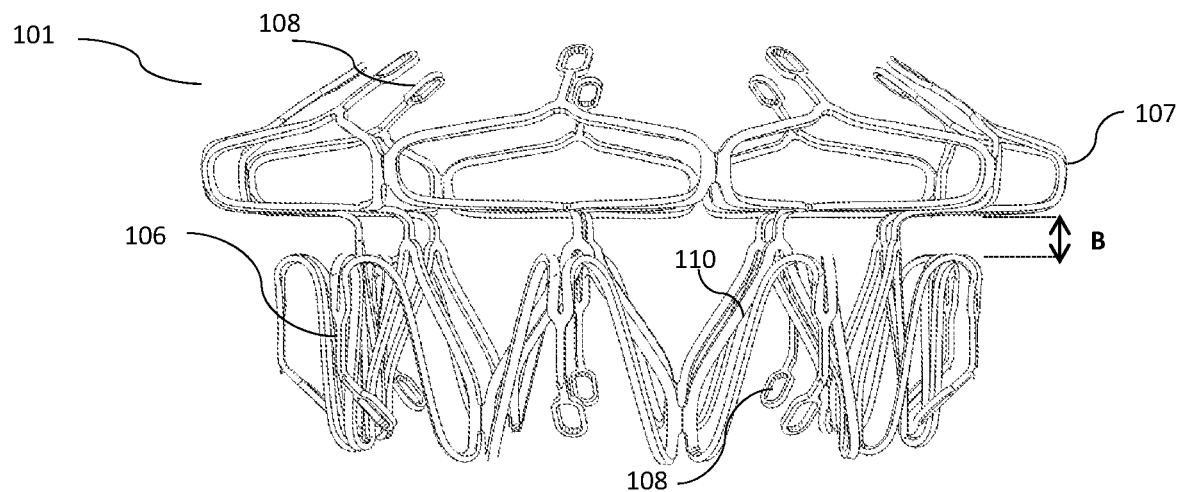
FIG. 3: a structure schematic view of an outer valve stent of the transapical implantable mitral valve device provided by the first embodiment of the present invention.

FIG. 2 is a structure schematic view of the transapical implantable mitral valve device provided in the first embodiment of the present invention implanted into the human body. FIG. 3 is a structure schematic view of the outer valve stent of the transapical implantable mitral valve device provided by the first embodiment of the present invention. As shown in FIGS. 1 to 3, the special contour shape of the outer valve stent 101 can be firmly anchored to the human mitral valve annulus. Moreover, the outer valve stent 101 provides radial support force for the mitral valve annulus, and can grasp the diseased mitral valve leaflet of human body and fix it on the mitral valve annulus. Specifically, in this embodiment, the outer valve stent 101 includes an outer valve stent body of an annular network structure that is composed of a plurality of first structure units 110 arranged in a circumferential direction, which provides radial support force for the mitral valve annulus, so that the valve device can be positioned in the mitral valve annulus. In the present embodiment, the first structure units 110 may be a diamond shape defined by stent rods; it also can be a square, circular, rectangular or other shape, but the diamond shape is preferable. These shapes allow the valve stent to be stretched axially while being compressed radially for easy delivery into the body. The outer valve stent 101 also includes an anchoring unit for anchoring the mitral valve device, which anchors the mitral valve device at the mitral valve annulus in combination with the radial support force of the outer valve stent body.

As shown in FIG. 3, in this embodiment, the anchoring unit includes an U-shaped structure unit 107 and an S-shaped structure unit 106. The U-shaped structure unit 107 and the S-shaped structure unit 106 can grasp the diseased mitral valve leaflet of human body and fix it on the mitral valve annulus. The mitral valve device is implanted into the patient, the U-shaped structure unit 107 is close to the left atrial end of the patient, and the S-shaped structure unit 106 is close to the left ventricular end of the patient. Therefore, in this specification, when the mitral valve device is implanted into the patient, the end of the U-shaped structure unit of the mitral valve device is also called the left atrial end (or head end) of the mitral valve device, and the end of the S-shaped structure unit of the mitral valve device is also called the left ventricular end (or tail end) of the mitral valve device. In addition, in this specification, it is defined that after the mitral valve device is implanted into the patient, the surface of the mitral valve device that contacts the heart tissue is the outer surface (or exterior, outside surface, outside) of the mitral valve device; corresponding to the outer surface, the surface of the mitral valve device providing the prosthetic valve leaflet structure is the inner surface (or interior, inside surface, inside) of the mitral valve device. In addition, as shown in FIG. 3, it is defined in the specification that the direction from the left atrial end (or head end) to the left ventricular end (or tail end) of the mitral valve device in FIG. 3 is vertical direction (or axial direction), and the corresponding direction perpendicular to the vertical direction is horizontal direction (or radial direction).

As shown in FIGS. 1 to 3, in this embodiment, the number of the first structure units 110 is between 6 and 15. Preferably, the number of the first structure units 110 is between 9 and 12. In this embodiment, the left atrial end of each first structure unit 110 is connected with one U-shaped structure unit 107 whose opening is toward the interior of the mitral valve device. Therefore, the U-shaped structure unit 107 is also arranged in the circumferential direction to form a ring. As shown in FIG. 2, the annularly arranged U-shaped structure unit 107 can be positioned at the left atrial end of the human mitral valve annulus, so that the mitral valve device cannot move to the left ventricular end, thus further fixing the position of the mitral valve device. In this embodiment, the S-shaped structure unit 106 is formed by bending the left ventricular end of each first structure unit 110 outwards to form an S-shaped structure. As shown in FIG. 2, the S-shaped structure unit 106 can grasp the diseased mitral valve leaflet of human body and further fix the mitral valve device on the mitral valve annulus. As shown in FIG. 3, in this embodiment, both a terminal of the U-shaped structure unit 107 near the left atrial end and a terminal of the S-shaped structure unit 106 near the left ventricular end are provided with pull rings 108. Alternatively, the shape of the pull rings 108 may be a circle, a rounded rectangle, etc., preferably a rounded rectangle. The pull rings 108 can fix the mitral valve device on a delivery system, which is convenient for transferring the mitral valve device into the human body.

Figure 4:
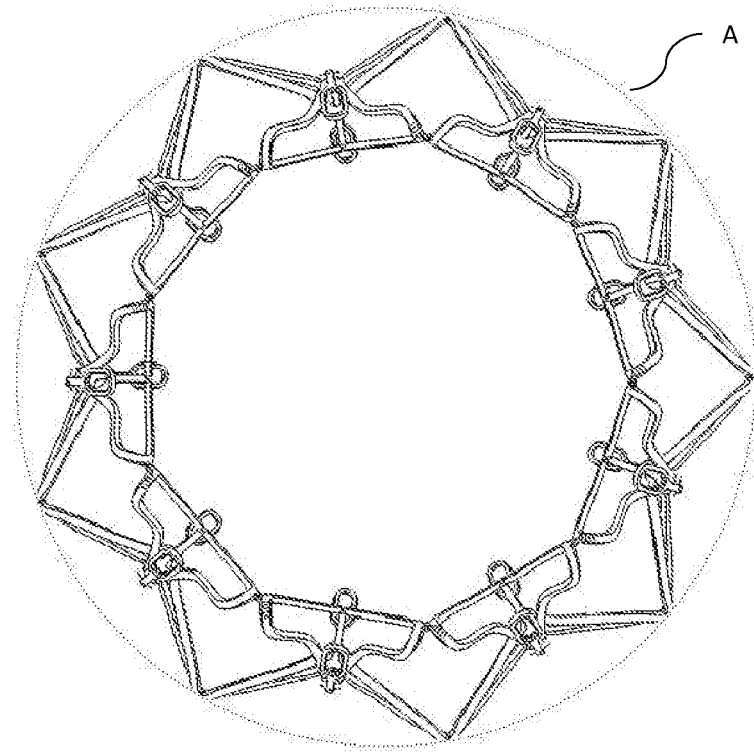
FIG. 4: a top schematic view of the outer valve stent of the transapical implantable mitral valve device provided by the first embodiment of the present invention.

FIG. 4 is a top schematic view of the outer valve stent of the transapical implantable mitral valve device provided by the first embodiment of the present invention. As shown in FIG. 4, the largest circumscribed circle A (i.e. the large circle of the ring) of the plurality of U-shaped structure units 107 which form the ring has a diameter between 55 mm and 65 mm, and the diameter range can make the mitral valve device unable to move from the left atrial end to the left ventricle through the mitral semi-annulus. At the same time, in this embodiment, when using the mitral valve device, the depth of the whole mitral valve device invading the left atrium is less than 15 mm; the depth of the whole mitral valve device invading the left ventricle is less than 25 mm. Preferably, the depth of the invasion into the left atrium ranges between 6 mm and 12 mm, and the depth of the invasion into the left ventricle ranges between 11 mm and 21 mm. The invasion depth of the above-mentioned mitral valve device is determined by the overall length of the outer valve stent in the axial direction. Therefore, the overall length ranges between 17 mm and 33 mm, and said appropriate length can make the mitral valve device placed in the valve leaflet and avoid touching the tissue in the ventricle.

As shown in FIG. 3, the vertical distance B between the horizontal plane on which the endpoint of the S-shaped structure unit 106 near the left atrial end locates and the horizontal plane on which the endpoint of the U-shaped structure unit 107 near the left ventricular end locates is between 0.5 mm and 4 mm, preferably between 1 mm and 3 mm. The above-mentioned gap between the U-shaped structure unit and the S-shaped structure unit forms a shape of a C-shaped clip. When in use, the gap is clamped at the valve annulus to fix the mitral valve device.

The S-shaped structure unit 106 shall be as close as possible to the body composed of the first structure units 110 in the horizontal direction, that is, the thickness of the S-shaped structure unit 106 in the radial direction shall be as small as possible. Specifically, the thickness of the S-shaped structure unit 106 in the radial direction is 0.5 mm to 4 mm, which can ensure that the mitral valve device does not touch the tissue in the ventricle.

Figure 5:
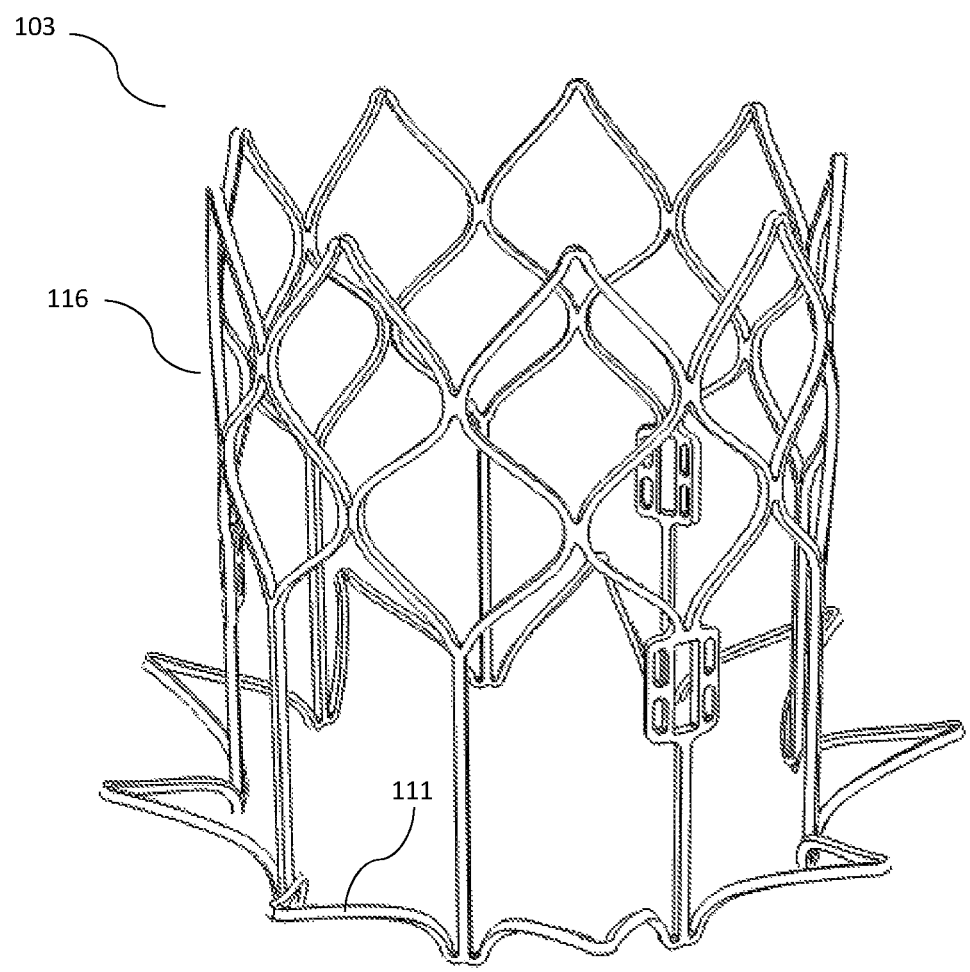
FIG. 5: a structure schematic view of an inner valve stent of the transapical implantable mitral valve device provided by the first embodiment of the present invention.

FIG. 5 is a structure schematic view of the inner valve stent of the transapical implantable mitral valve device provided by the first embodiment of the present invention. As shown in FIG. 5, in this embodiment, the inner valve stent 103 is an interventional mitral valve stent. Specifically, the inner valve stent 103 includes a plurality of second structure units 116 which are arranged along the circumferential and axial directions to form an inner valve stent body of a circular network structure. In the present embodiment, the second structure unit 116 may be a diamond shape defined by stent rods; it also can be a square, circular, rectangular or other shape, but a diamond shape is preferable. These shapes allow the valve stent to be stretched axially while being compressed radially for easy delivery into the body. The tail ends of the plurality of second structure units 116 close to the left ventricular end extend and turn out to form first connecting structures 111. The diameter of circumscribed circle of the plural first connecting structures 111 formed through turning out is consistent with the inner diameter of the outer valve stent body, so that when the inner valve stent 103 is placed inside the outer valve stent 101, the plurality of first connecting structures 111 can be in contact with the inner wall of the outer valve stent body, which further facilitates fixation of the two. The inner valve stent 103 and the outer valve stent 101 are rigidly connected by the first connecting structures 111. Because the first connecting structures 111 are formed by turning out the second structure units 116, there is a certain distance between the inner wall of the outer valve stent and the outer wall of the inner valve stent, and a cavity is formed, which cavity can prevent impact on the inner valve stent when the outer valve stent is deformed. Preferably, the number of the second structure units 116 arranged in the circumferential direction is the same as the number of the first structure units 110.

Specifically, as shown in FIG. 2, in the radial direction, there is a certain distance between the outer valve stent 101 and the inner valve stent 103, forming a cavity 154. The outer valve stent 101 will be deformed by compression of the irregular mitral valve annulus in the human body, while the cavity 154 can provide a buffer space to keep the shape of the valve leaflet structure 102 always unchanged. In this embodiment, in the radial direction, there is a certain distance between the outer valve stent 101 and the inner valve stent 103 which is not less than 1.5 mm, that is, the thickness of the cavity formed between the outer valve stent 101 and the inner valve stent 103 in the radial direction is not less than 1.5 mm. Preferably, the thickness of the cavity in the radial direction is 3 mm to 8 mm.

Alternatively, as shown in FIG. 5, in this embodiment, the first connecting structure 111 is a triangular structure or other shaped structure formed by turning out the left ventricular end of the second structure units 116. The number of the first connecting structures 111 is between 6 and 15, preferably 9 or 12, that is, the number of the second structure units 116 arranged in the circumferential direction. Further, as shown in FIG. 1, in this embodiment, a layer of outer skirt 104 is wrapped on the inner surface and/or outer surface of the outer valve stent 101, and the outer skirt 104 is laid flat around the surface of the outer valve stent 101 to cover a circle and covers the first connecting structure 111 of the inner valve stent 103 at the same time, and is fixed by means of suturing, pressing or bonding, etc. The inner surface and/or outer surface of the inner valve stent 103 is wrapped with a layer of inner skirt 105, which is laid flat around the surface of the inner valve stent 103 to cover a circle, and is fixed by means of suturing, pressing or bonding, etc. The valve leaflet structure 102 is fixed on the inner skirt 103 by suturing to replace the in-situ mitral valve diseased in human body. The inner valve stent 103 and the outer valve stent 101 are rigidly connected by the first connecting structures 111, and at the same time, they are flexibly connected by the outer skirt 104. Therefore, the outer skirt 104 and the inner skirt 105 are arranged so that the blood flowing from the left atrium to the left ventricle can only pass through the valve leaflet structure 102 of the inner valve stent 103 when passing through the mitral valve device, but not through the other parts of the mitral valve device, that is to avoid peripheral leakage.

In this embodiment, material of the valve leaflet structure is animal pericardium or polymer material. Preferably, material of the valve leaflet structure is bovine pericardium, pig pericardium, polytetrafluoroethylene, fiber cloth or fiber membrane. In this embodiment, material of the outer skirt is animal pericardium or polymer material. Preferably, material of the outer skirt is bovine pericardium, pig pericardium, polytetrafluoroethylene, fiber cloth or fiber membrane.

In this embodiment, material of the inner skirt is animal pericardium or polymer material. Preferably, material of the inner skirt is bovine pericardium, pig pericardium, polytetrafluoroethylene, fiber cloth or fiber membrane.

Figure 6:
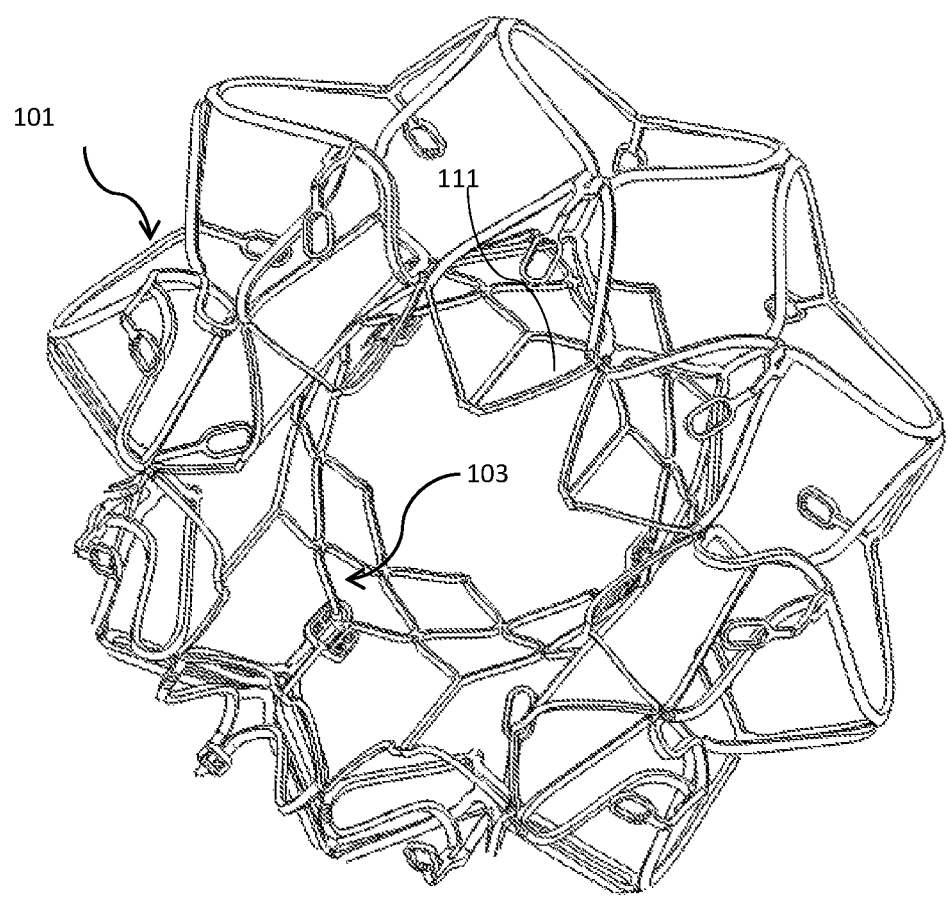
FIG. 6: a three-dimensional structure schematic view of an assembly manner for the outer valve stent and the inner valve stent of a transapical implantable mitral valve device provided by the first embodiment of the present invention.
Figure 7:
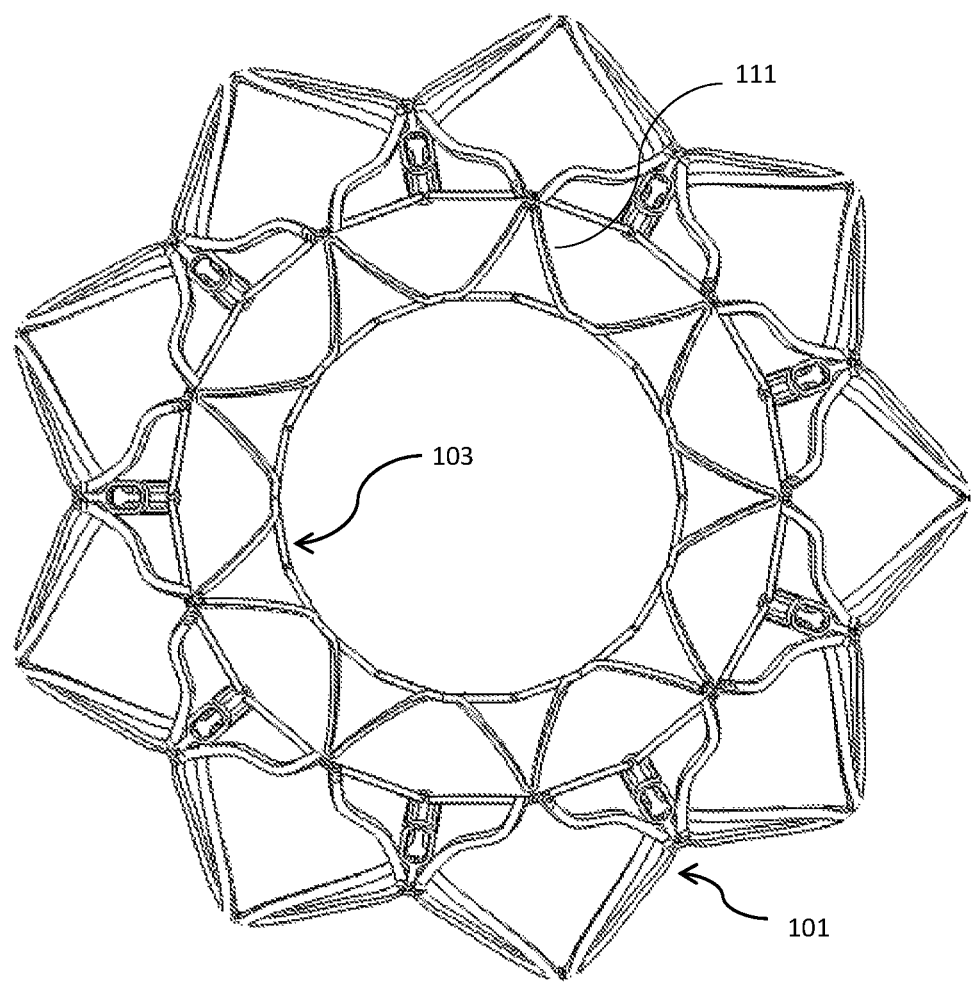
FIG. 7: a schematic top view of the assembly manner of FIG. 6.
Figure 8:
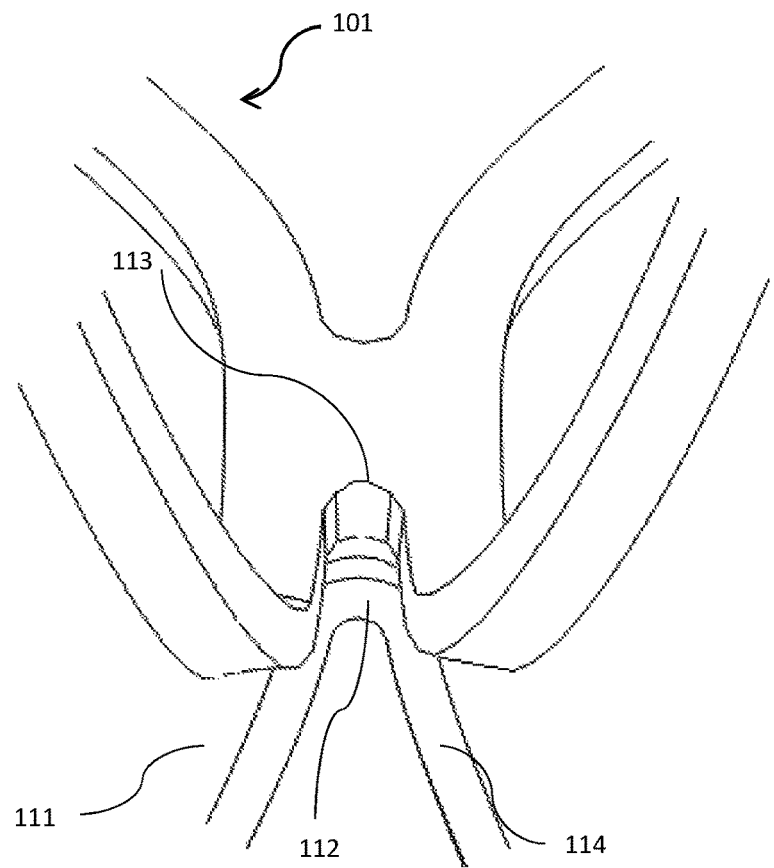
FIG. 8: a partial schematic view of a connecting portion of a kind of rigid connection of the assembly manner of FIG. 6.

FIG. 6 is a three-dimensional structure schematic view of an assembly manner for the outer valve stent and the inner valve stent of the transapical implantable mitral valve device provided by the first embodiment of the present invention; FIG. 7 is a top schematic view of the assembly manner of FIG. 6. FIG. 8 is a partial schematic view of connecting portion of a kind of rigid connection of the assembly manner of FIG. 6. As shown in FIG. 6, FIG. 7 and FIG. 8, the first connecting structure 111 formed by turning out the inner valve stent 103 includes two first straight rods 114 which intersect to form a first vertex 112. Accordingly, there is a structure unit joint 113 between the adjacent first structure units 110 of the outer valve stent 101. After the inner valve stent 103 is placed into the inner valve stent, the first vertex 112 corresponds to and contacts with the structure unit joint 113, and the two are fixed by means of suturing, pressing or bonding, etc., so that the inner valve stent 103 is connected with the outer valve stent 101 (as shown in FIG. 7).

Figure 9:
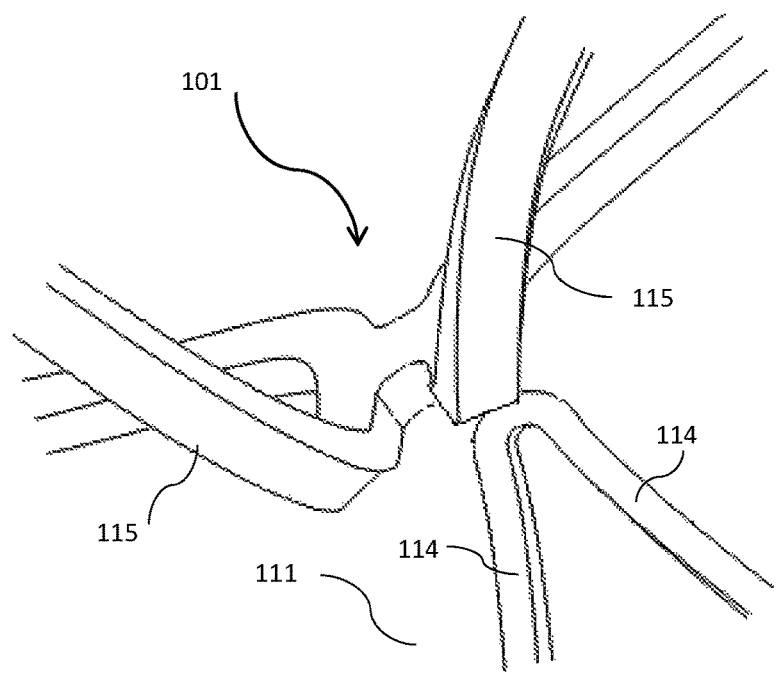
FIG. 9: a partial schematic view of a connecting portion of another kind of rigid connection of the assembly manner of FIG. 6.

FIG. 9 is a partial schematic view of a connecting portion of another kind of rigid connection of the assembly manner of FIG. 6. As shown in FIG. 9, there is a structure unit joint between the adjacent first structure units 110 of outer valve stent 101, and the left ventricular end of the structure unit joint includes respective second straight rods 115 of two adjacent first structure units 110. As shown in FIG. 9, in this embodiment, one of the second straight rods 115 is aligned with one of the first straight rods 114, and the first straight rod 114 and the second straight rod 115 are fixed by means of suturing, pressing or bonding, etc., so that the inner valve stent 103 is connected with the outer valve stent 101. The rigid connection described above is achieved by contacting the stent rod of the outer valve stent with the stent rod of the inner valve stent; therefore, the combination manner between the second straight rod 115 and the first straight rod 114 is not limited to the above exemplary ways.

Alternatively, the above first straight rod 114 may be in a straight line shape, and the first straight rod 114 may also be in an arc shape.

Alternatively, in the present embodiment, as previously described, the outer skirt 104 is laid flat around the surface of the outer valve stent 101 to cover a circle, and covers the first connecting structure 111 of the inner stent 103 at the same time, which is used as a flexible connection. In addition, on such basis, joint skirt is sutured on the inside or outside of the first connecting structure 111 simultaneously, which is further used as a flexible connection to play a reinforcing role. In other embodiments, the joint skirt may also not be added. The skirt of the flexible connection can play the role of strengthening and blocking the blood. Like the outer skirt and inner skirt, material of the joint skirt is animal pericardium or polymer material. Preferably, material of the joint skirt is bovine pericardium, pig pericardium, polytetrafluoroethylene, fiber cloth or fiber membrane.

In this embodiment, the outer valve stent 101 and the inner valve stent 103 are integrally made of hyperelastic alloy and/or shape memory alloy materials, in particular, formed by laser cutting pipes of such materials.

Figure 10:
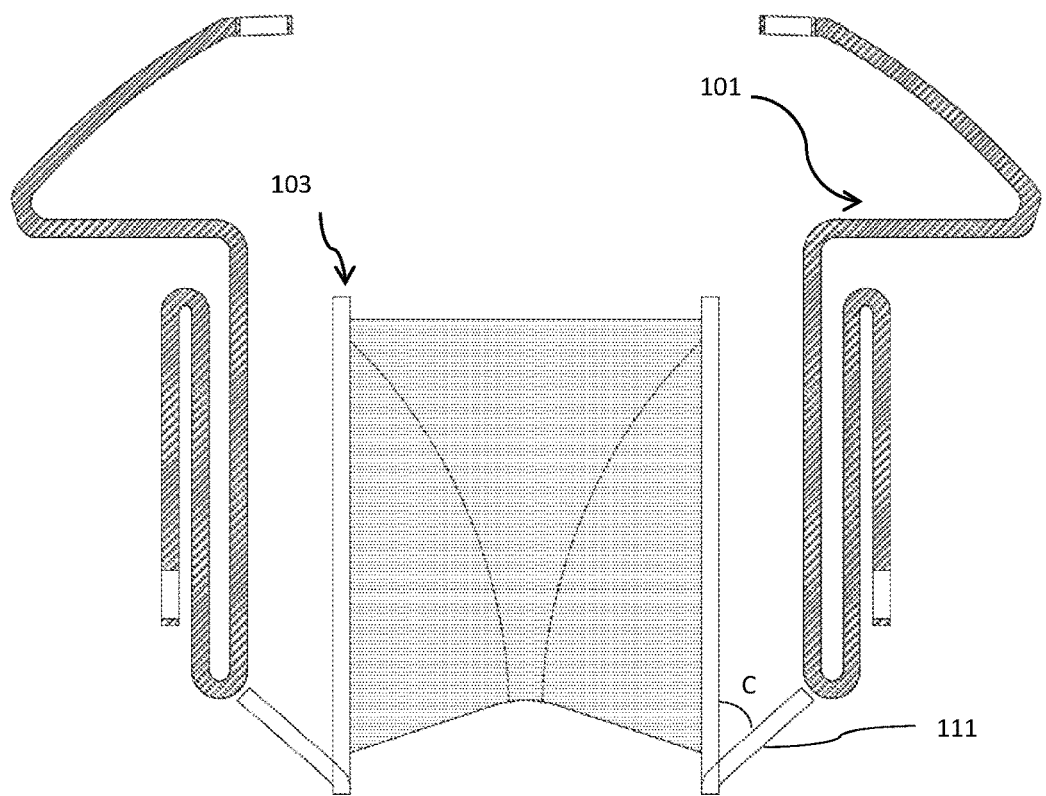
FIG. 10 and FIG. 11: structure schematic views of different assembly manners for the outer valve stent and the inner valve stent of the transapical implantable mitral valve device provided by the first embodiment of the present invention.
Figure 11:
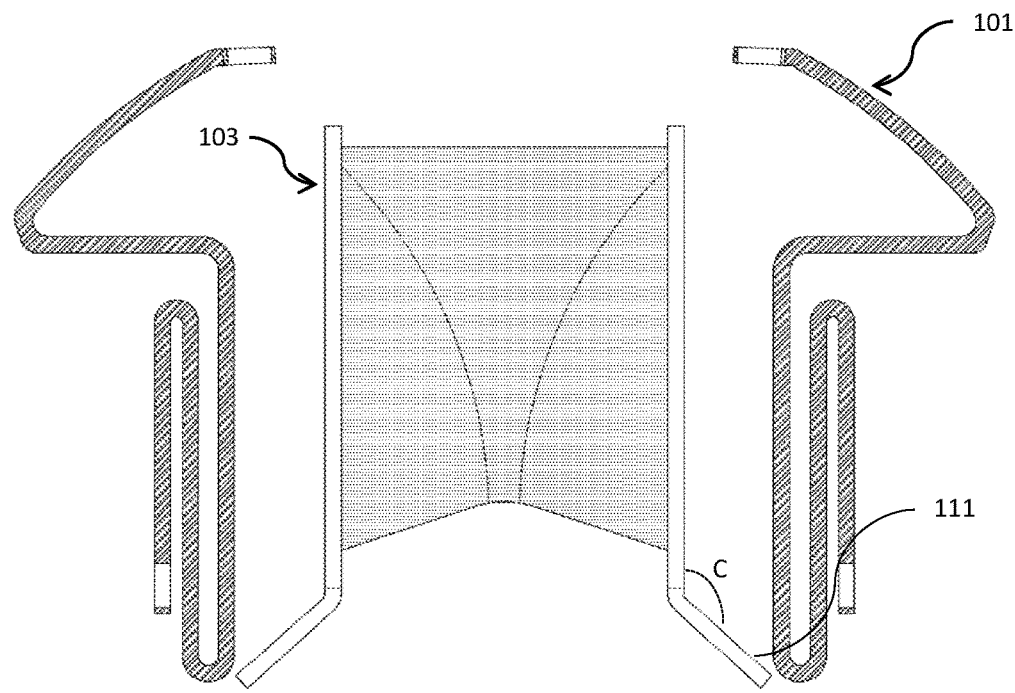

In order to ensure that the inner valve stent will not be compressed to deform by the diseased mitral valve annulus, the inner valve stent has a certain degree of freedom, that is, the position of the inner stent in the outer stent is not stationary, because the cavity between the inner valve stent and the outer valve stent can be deformed by force, so the contour of the inner valve stent is not affected and its function is guaranteed. The first connecting structure 111 of a triangular shape or other shape formed by turning out the second structure units has an out-turning angle C of between 15 degrees and 165 degrees (see FIG. 10 and FIG. 11). The out-turning angle refers to the angle formed by the line connecting the terminal of the first connecting structure 111 with the place where it turns out and bends with respect to the vertical direction, see FIG. 10 and FIG. 11. As mentioned previously, in the radial direction, there is a certain distance between the outer valve stent 101 and the inner valve stent 103 (that is, to form a cavity), which can buffer the impact on the inner stent due to compression deformation of the outer stent.

Embodiment 2

Figure 12:
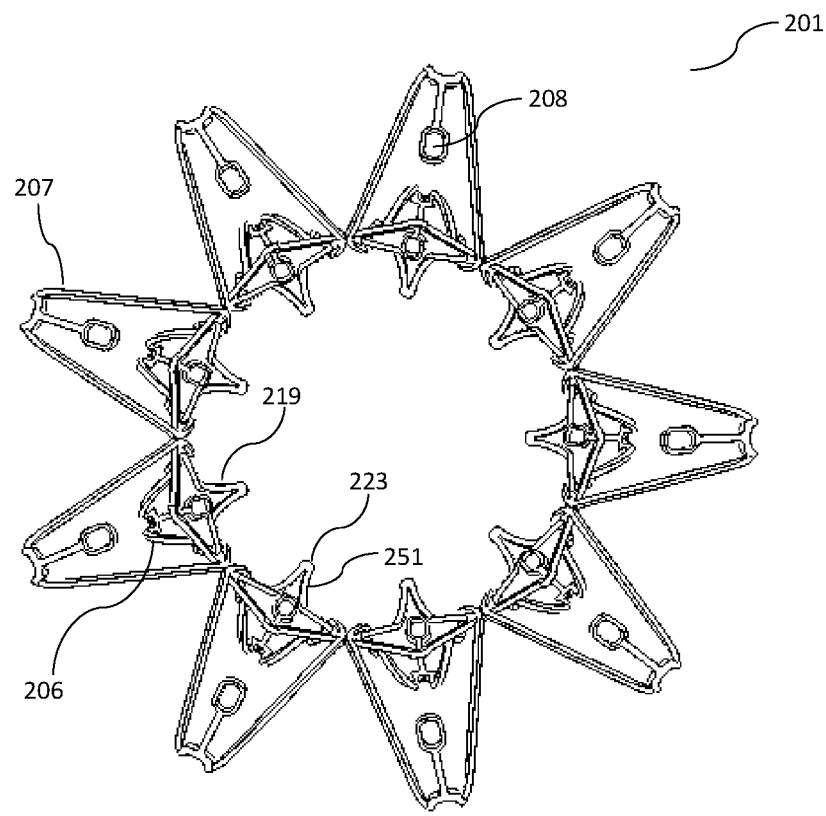
FIG. 12: a top schematic view of an outer valve stent of a transapical implantable mitral valve device provided by the second embodiment of the present invention.
Figure 13:
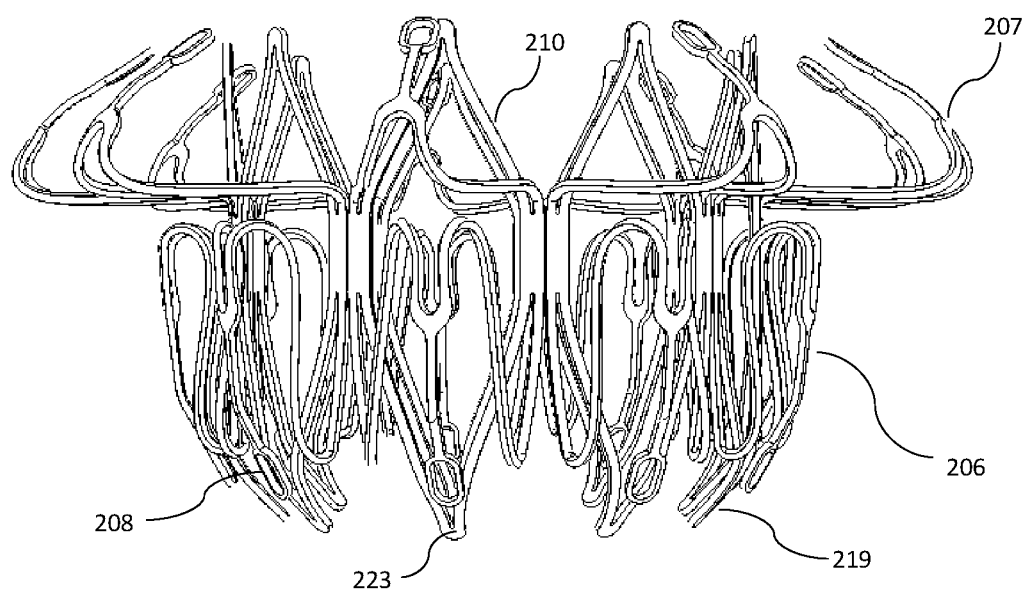
FIG. 13: a structure schematic view of an outer valve stent of the transapical implantable mitral valve device provided by the second embodiment of the present invention.

FIG. 12 is a top schematic view of the outer valve stent of the transapical implantable mitral valve device provided by the second embodiment of the present invention; and FIG. 13 is a structure schematic view of the outer valve stent of the transapical implantable mitral valve device provided by the second embodiment of the present invention. As shown in FIG. 12 and FIG. 13, in this embodiment, the outer valve stent 201 provides radial support force for the mitral valve annulus, and can grasp the diseased mitral valve leaflet of human body and fix it on the mitral valve annulus. Specifically, the outer valve stent 201 includes a body of annular network structure that is composed of a plurality of first structure units 210 arranged in the circumferential direction to provide radial support force for the mitral valve annulus, and an U-shaped structure unit 207 and an S-shaped structure unit 206 which play an anchoring effect on the mitral valve device. The U-shaped structure unit 207 and the S-shaped structure unit 206 can grasp the diseased mitral valve leaflet of human body and fix it on the mitral valve annulus.

In the present embodiment, the number of the first structure units 210 ranges between 6 and 15. Preferably, the number of the first structure units 210 is between 9 and 12. In the present embodiment, two adjacent first structure units 210 form a structure unit joint, and two adjacent structure unit joints are connected with a U-shaped structure unit 207 along the left atrial end, whose opening is toward the inside of the mitral valve device, and is connected with the S-shaped structure unit 206 along the left ventricular end. The U-shaped structure unit 207 and the S-shaped structure unit 206 can grasp the diseased mitral valve leaflet of human body and fix it on the mitral valve annulus.

As shown in FIG. 12 and FIG. 13, in the present embodiment, the end of the first structure unit 210 of the outer valve stent 201 close to the left ventricle folds toward the interior of the mitral valve device, forming an in-turning triangular second connecting structure 219. The diameter of the inscribed circle of the plurality of second connecting structures 219 formed through turning in is consistent with the outer diameter of the inner valve stent body, so that the plurality of second connecting structures 219 can be in contact with the outer wall of the inner valve stent body.

Figure 14:
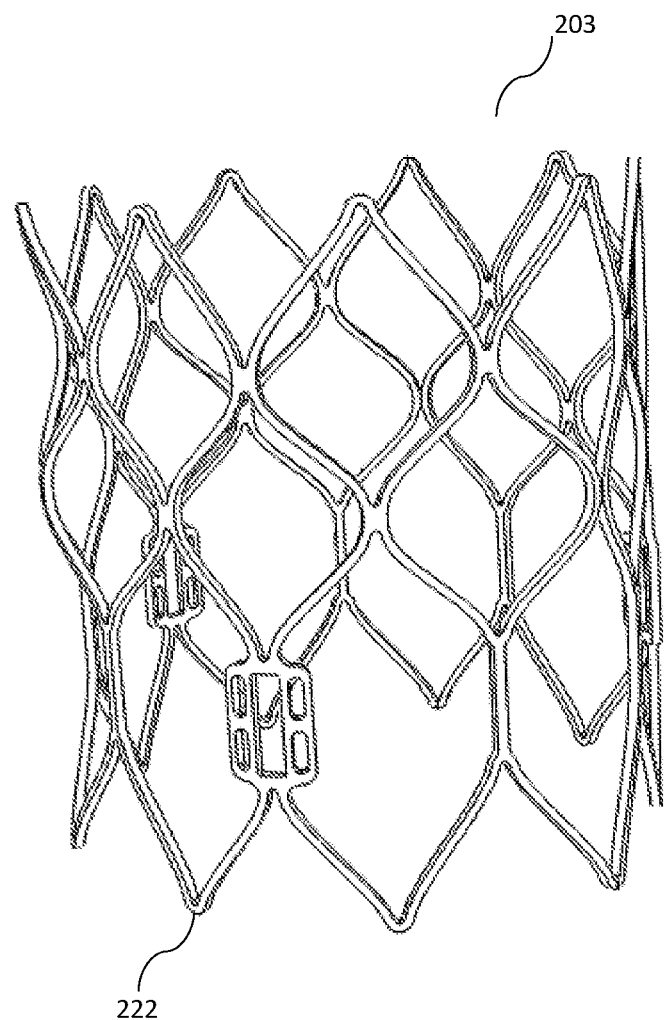
FIG. 14: a structure schematic view of an inner valve stent of the transapical implantable mitral valve device provided by the second embodiment of the present invention.

FIG. 14 is a structure schematic view of the inner valve stent of the transapical implantable mitral valve device provided by the second embodiment of the present invention. As shown in FIG. 14, the inner valve stent 203 in this embodiment has a structure basically similar to that of the inner valve stent in Embodiment 1, but the end of the second structure unit close to the left ventricle in this embodiment does not turn out.

Figure 15:
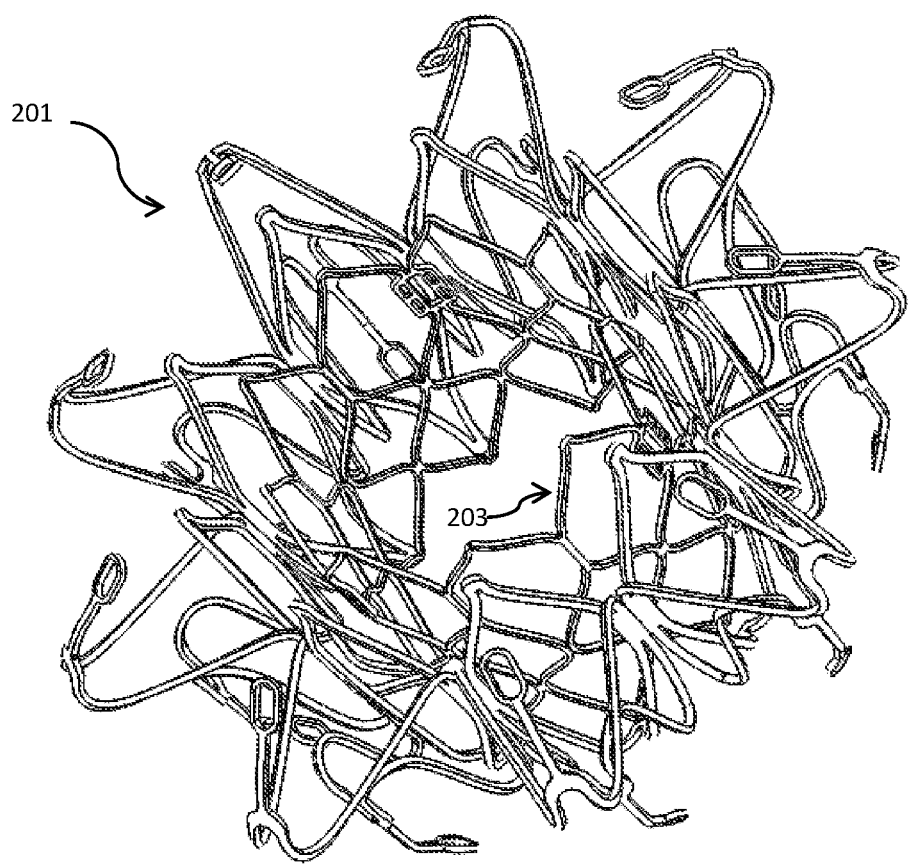
FIG. 15: a three-dimensional structure schematic view of an assembly manner for the outer valve stent and the inner valve stent of the transapical implantable mitral valve device provided by the second embodiment of the present invention.
Figure 16:
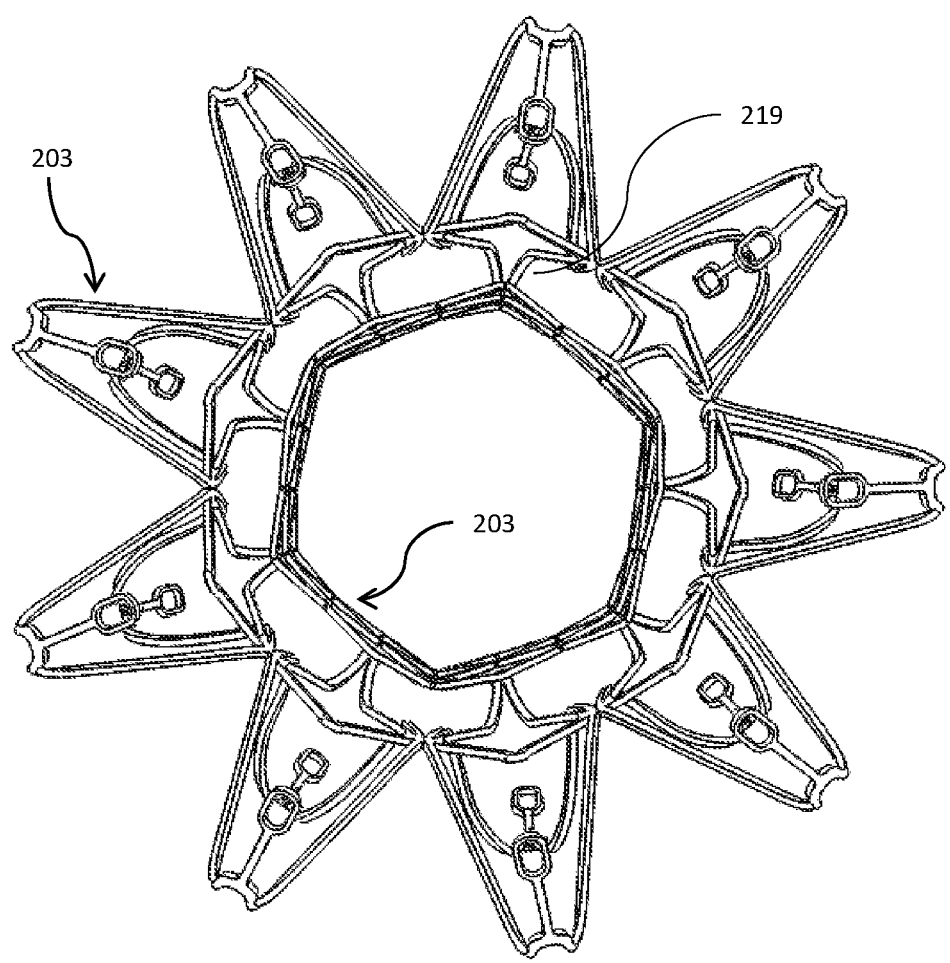
FIG. 16: a top schematic view of the assembly manner of FIG. 15.

FIG. 15 is a three-dimensional structure schematic view of the assembly manner for the outer valve stent and the inner valve stent of the transapical implantable mitral valve device provided by the second embodiment of the present invention; and FIG. 16 is a top schematic view of the assembly manner of FIG. 15. As shown in FIGS. 14, 15 and 16, the tip 222 of the inner valve stent 203 close to the left ventricular end is aligned with the second vertex 223 of the in-turning triangular second connecting structure 219 of the outer valve stent 201 close to the left ventricular end, and the tip 222 and the second vertex 223 are fixed by suturing, pressing or bonding, etc., so as to make the outer valve stent 201 and the inner valve stent 203 interconnected. In this embodiment, the second vertex 223 is formed by intersection of two sides (two third straight rods 251) of the same first structure unit 210 close to the left ventricular end (i.e., an angle of the diamond).

As in Embodiment 1, in this embodiment, a layer of outer skirt is wrapped on the inner surface and/or outer surface of the outer valve stent 201, the inner surface and/or outer surface of the inner valve stent 203 is wrapped with a layer of inner skirt, and the inner skirt and/or outer skirt can be covered to the second connecting structure 219 as a flexible connection. Alternatively, joint skirt can also be provided at the second connecting structure 219.

Figure 17:
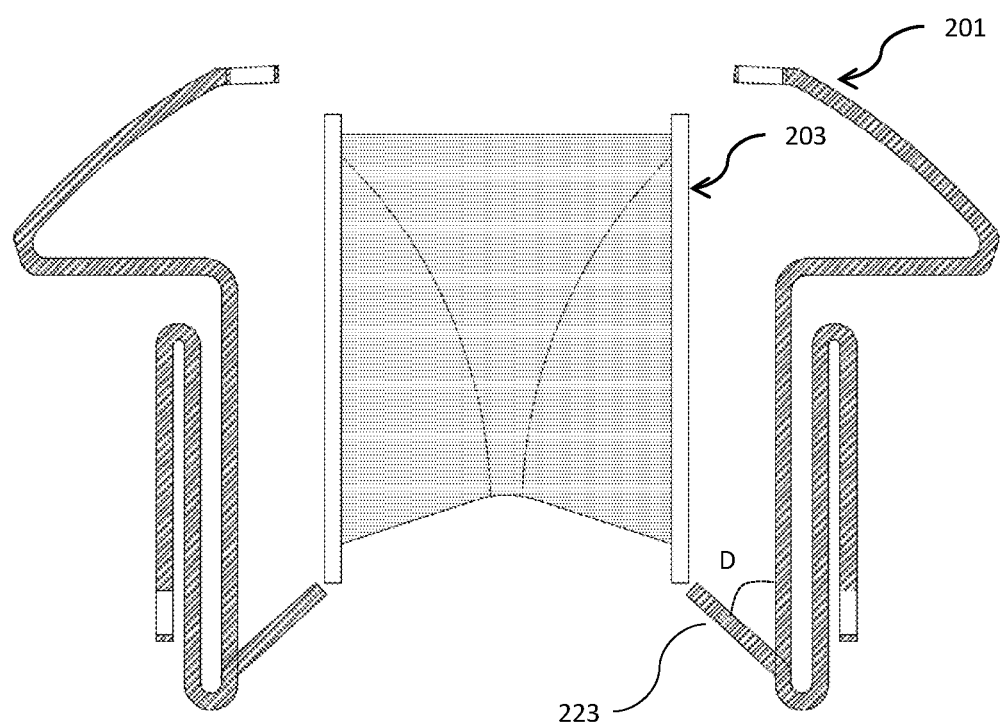
FIG. 17 and FIG. 18: structure schematic views of different assembly manners for the outer valve stent and the inner valve stent of the transapical implantable mitral valve device provided by the second embodiment of the present invention.
Figure 18:
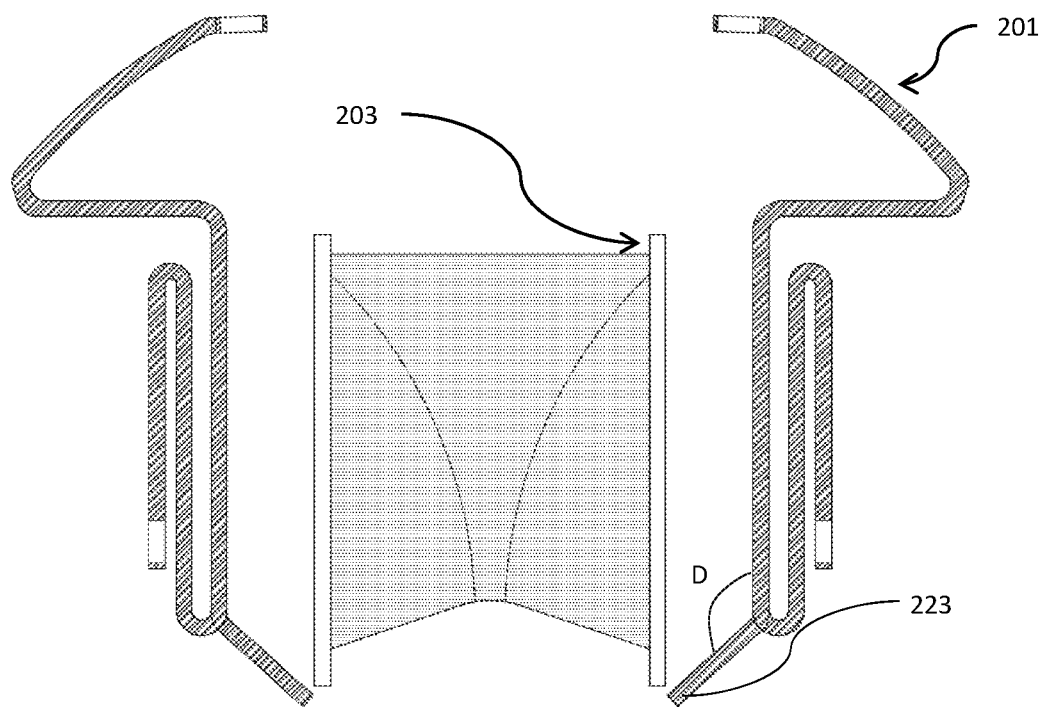

In this embodiment, the number of the second connecting structures 219 ranges between 6 and 15, preferably 9 or 12. In order to ensure that the inner stent will not be compressed to deform by the diseased mitral valve annulus, the inner valve stent has a certain degree of freedom, and the in-turning second connecting structure 219 of a triangle or other shapes of the first structure unit has an in-turning angle D between 15 degrees and 165 degrees. The in-turning angle refers to an angle formed by a line connecting the terminal of the second connecting structure 219 with the place where it turns in and bends with respect to the vertical direction (see FIG. 17 and FIG. 18). There is a certain distance between the outer valve stent 201 and the inner valve stent 203 (i.e. forming a cavity), which can buffer the impact on the inner stent due to compression deformation of the outer stent.

Other things not specifically described in this embodiment are the same as those in Embodiment 1, such as materials of various parts of the mitral valve device.

Embodiment 3

Figure 19:
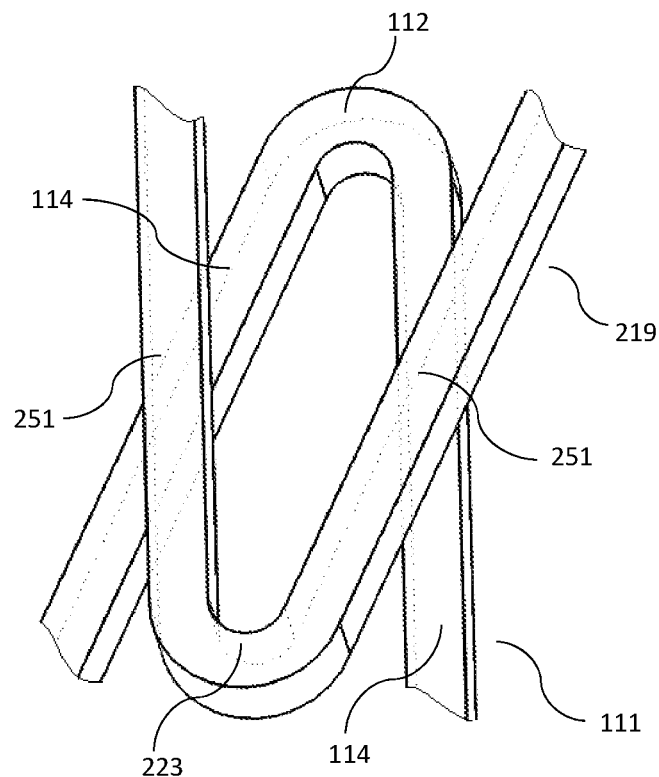
FIG. 19 to FIG. 21: a plurality of rigid connection combinations optional for an inner valve stent and an outer valve stent of the mitral valve device in the third embodiment of the present invention.
Figure 20:
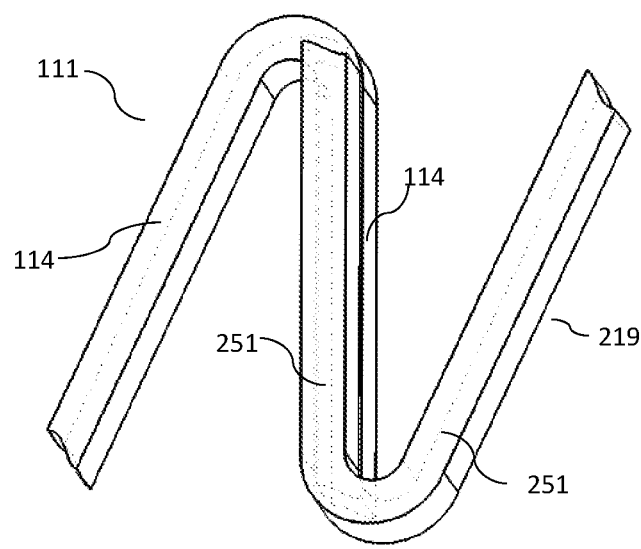
Figure 21:
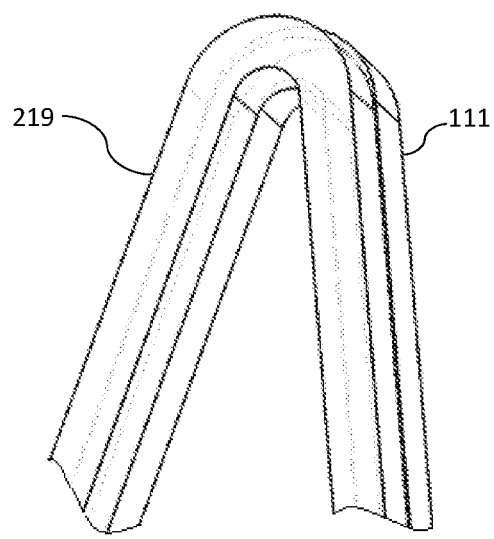
Figure 22:
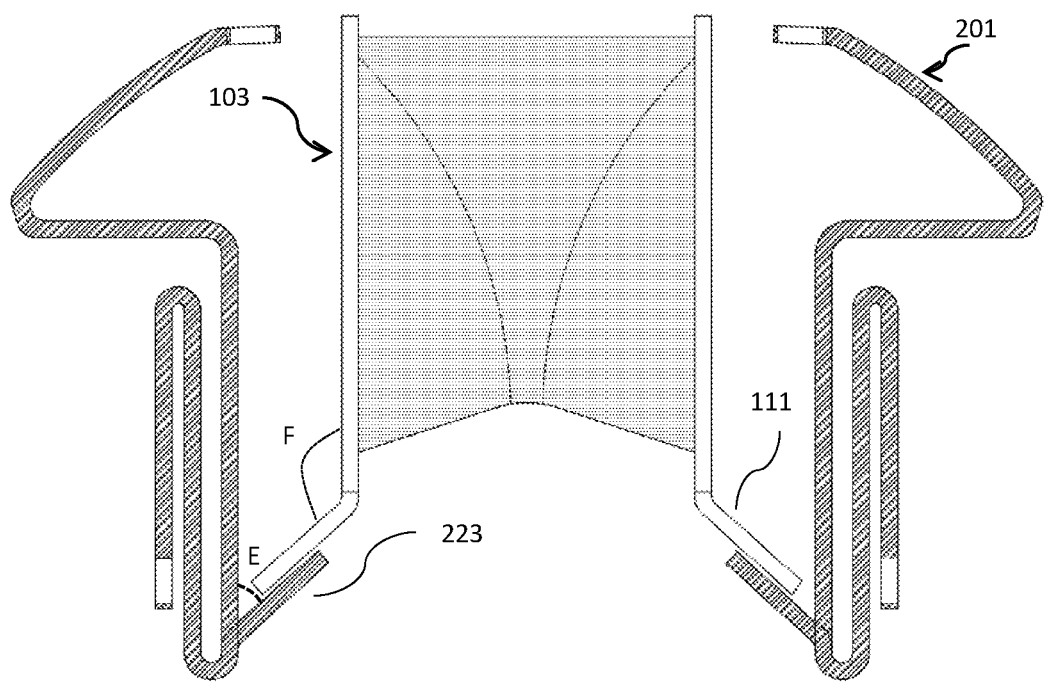
FIG. 22 to FIG. 25: structure schematic views of different assembly manners for the outer valve stent and the inner valve stent of the transapical implantable mitral valve device provided by the third embodiment of the present invention.
Figure 23:
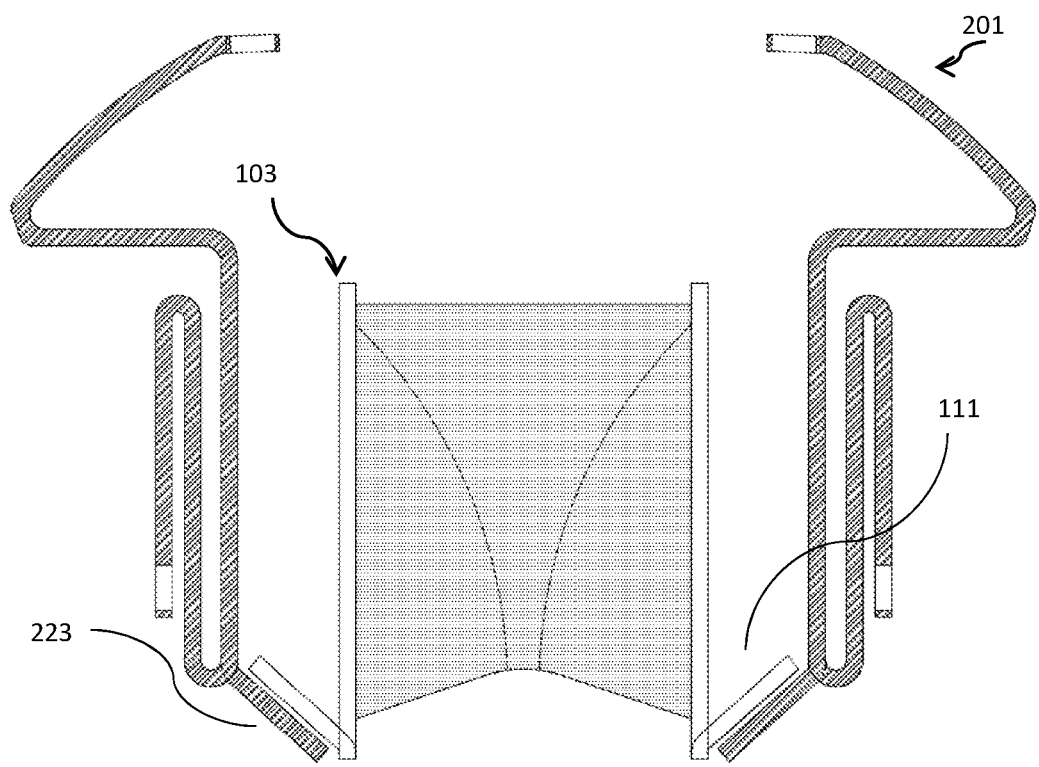
Figure 24:
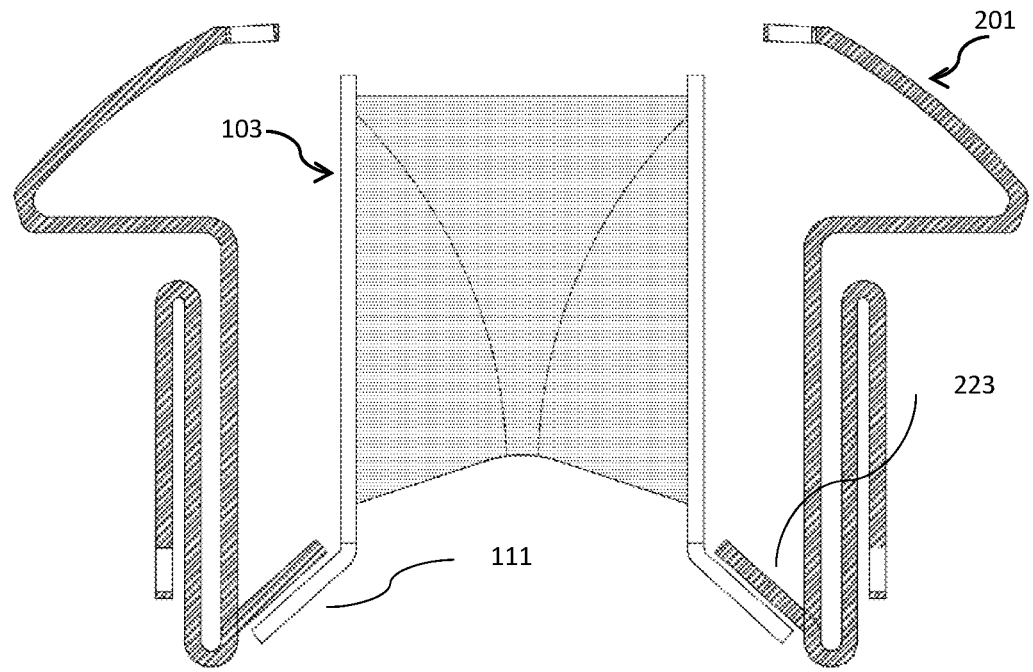
Figure 25:
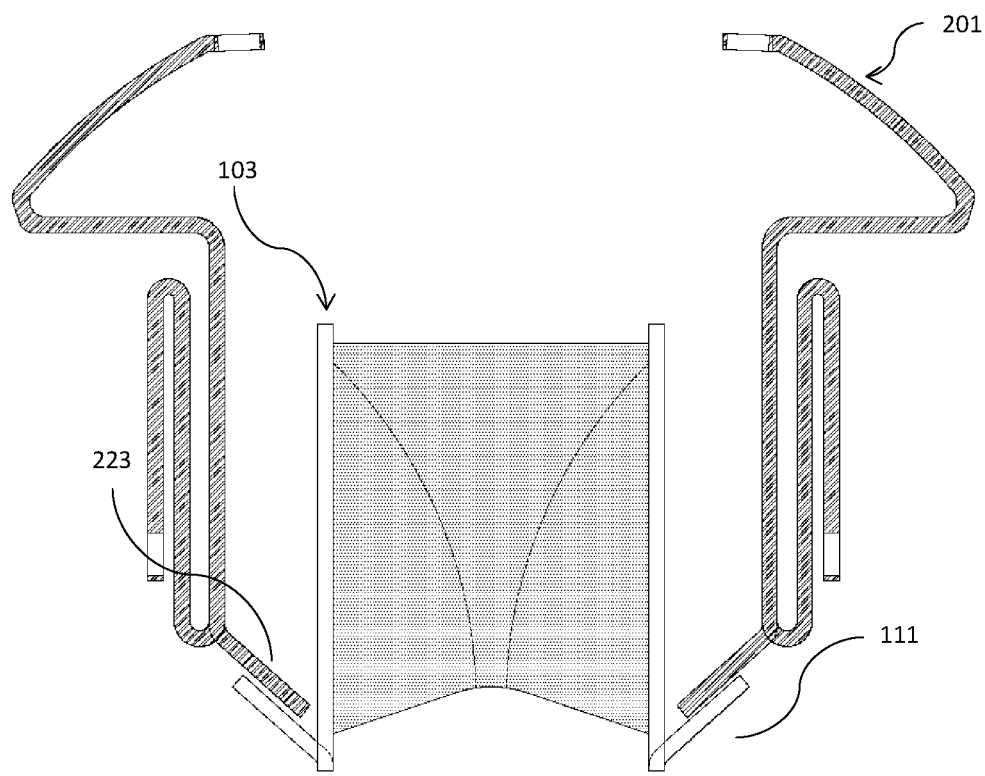

In the present embodiment, the inner valve stent of the transapical implantable mitral valve device is the same as that in Embodiment 1, and the outer valve stent is the same as that in Embodiment 2. FIGS. 19 to 21 show a plurality of rigid connection combinations optional for the inner valve stent and the outer valve stent of the mitral valve device in the third embodiment of the present invention. As shown in FIG. 19, the in-turning triangular second connecting structure 219 of the outer valve stent is overlapped with the out-turning triangular first connecting structure 111 of the inner valve stent; the third straight rod 251 of the outer valve stent intersects with the first straight rod 114 of the inner valve stent, enclosing to form a diamond shape, and the second vertex 223 of the in-turning triangular second connecting structure 219 of the outer valve stent and the first vertex 112 of the out-turning triangular first connecting structure 111 of the inner valve stent are located on a diagonal line of the diamond shape, and are fixed by suturing, pressing or bonding, etc.

Alternatively, as shown in FIG. 20, a third straight rod 251 of the in-turning triangular second connecting structure 219 of the outer valve stent coincides with a first straight rod 114 of the out-turning triangular first connecting structure 111 of the inner valve stent 103, and they are fixed by suturing, pressing or bonding, etc.

Alternatively, as shown in FIG. 21, the in-turning triangular second connecting structure 219 of the outer valve stent and the out-turning triangular first connecting structure 111 of the inner valve stent completely coincide, that is, the two first straight rods and the first vertex correspondingly coincide with the two third straight rods and the second vertex, and they are fixed by suturing, pressing or bonding, etc.

The first connecting structure 111 and the second connecting structure 219 have the same number which is between 6 and 15, preferably 9 or 12. In order to ensure that the inner stent will not be compressed to deform by the diseased mitral valve annulus, the inner stent has a certain degree of freedom. Both the in-turning angle E of the in-turning second connecting structure 219 of a triangle or other shape and the in-turning angle F of the out-turning first connecting structure 111 of a triangle or other shape are between 15 degrees and 165 degrees (see FIGS. 22 to 25). There is a certain distance between the outer valve stent and the inner valve stent (i.e. forming a cavity), which can buffer the impact on the inner stent due to compression deformation of the outer stent.

Other aspects not specifically described in this embodiment are the same as those in Embodiment 1, such as material of each part of the mitral valve device and provision of skirts, etc. In addition, in this embodiment, the joint skirt can be arranged on the outside or inside of the first connecting structure 111, or on the outside or inside of the second connecting structure 219, or the joint skirts are arranged on both the first connecting structure 111 and the second connecting structure 219, and the joint skirt can also be arranged between the first connecting structure 111 and the second connecting structure 219.

Embodiment 4

Figure 26:
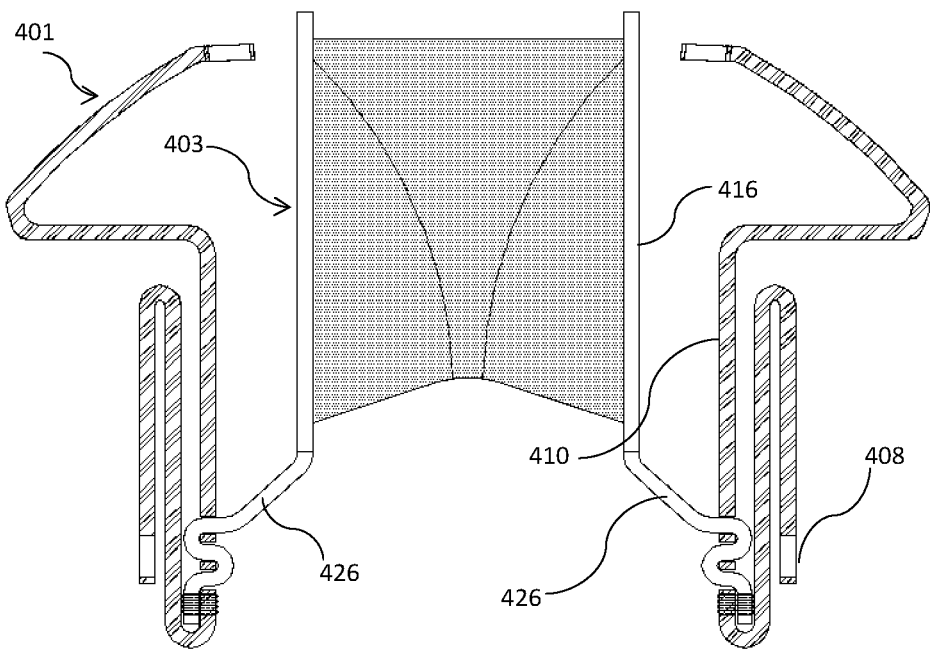
FIG. 26: a structure schematic view of a rigid connection of a assembly manner optional for an outer valve stent and an inner valve stent of a transapical implantable mitral valve device provided by the fourth embodiment of the present invention.

FIG. 26 is a structure schematic view of a rigid connection of the assembly manner optional for the outer valve stent and the inner valve stent of the transapical implantable mitral valve device provided by the fourth embodiment of the present invention. As shown in FIG. 26, the inner valve stent 403 includes a plurality of second structure units 416, which are arranged in the circumferential and axial directions to form an inner valve stent body of annular network structure. In the present embodiment, a filamentous connecting structure 426 is also provided on the end of the plurality of or each second structure unit 416 near the left ventricular.

Figure 28:
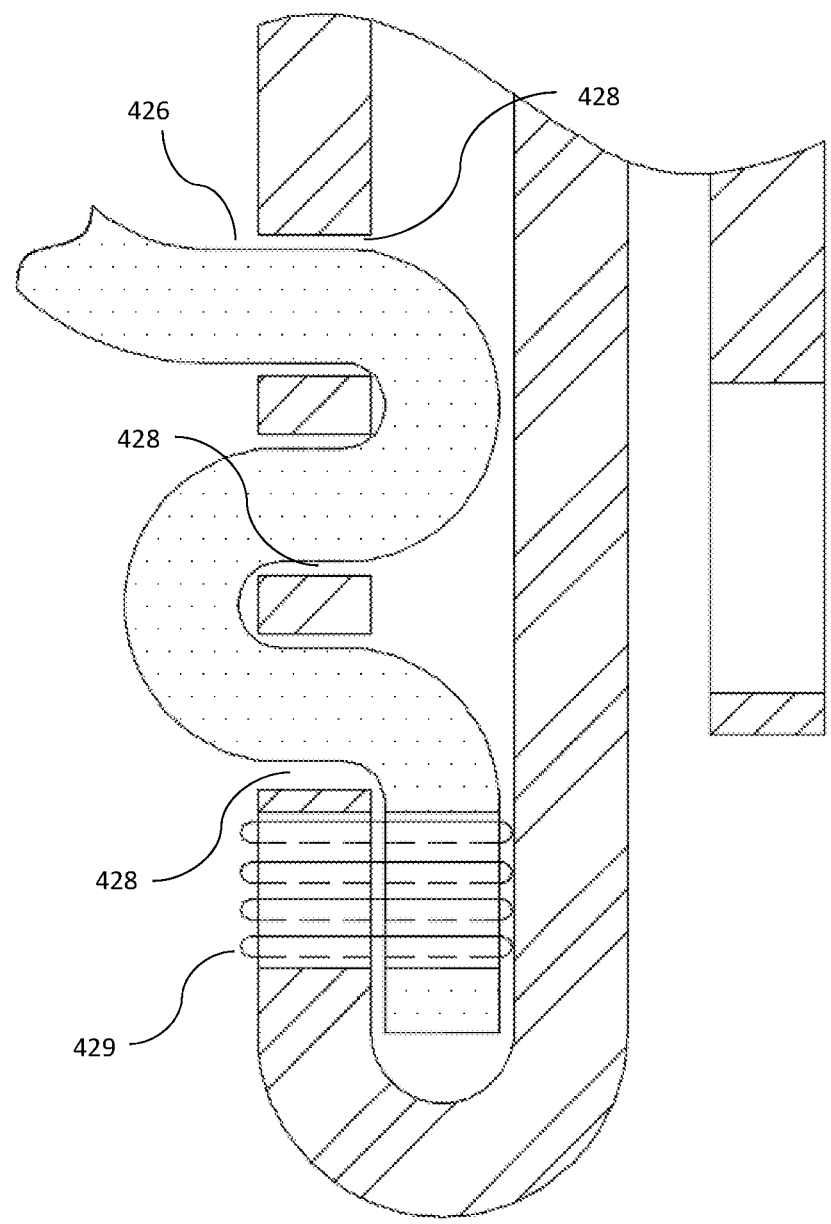
FIG. 28 to FIG. 30: detailed structure schematic views of the rigid connection of the assembly manner optional for the outer valve stent and the inner valve stent of the transapical implantable mitral valve device provided by the fourth embodiment of the present invention.
Figures 29, 30:
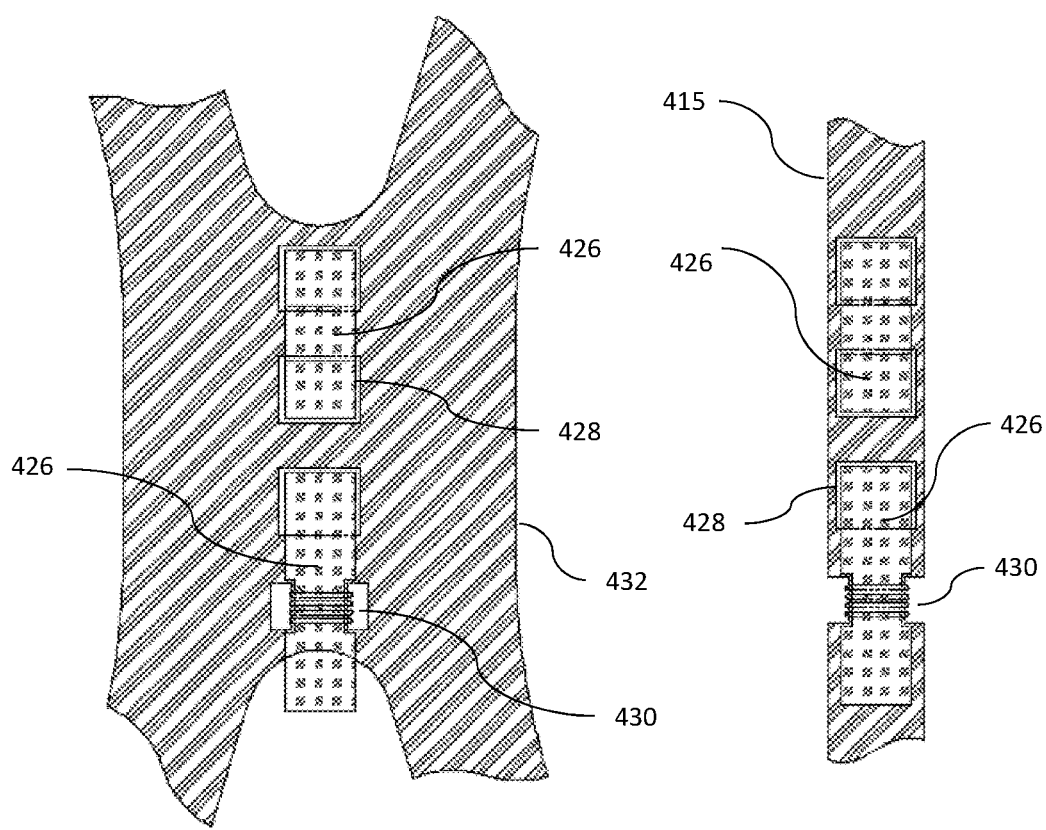
Figure 31:
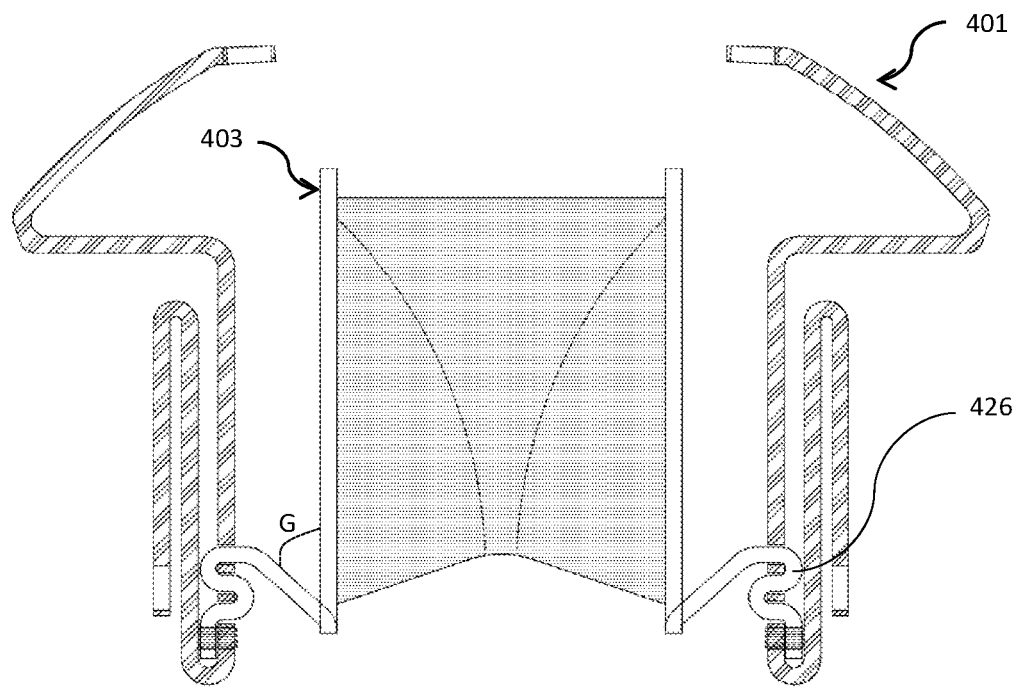
FIG. 31: a structure schematic view of other assembly manners optional for the outer valve stent and the inner valve stent of the transapical implantable mitral valve device provided by the fourth embodiment of the present invention.

In the present embodiment, the contour shape of the outer valve stent 401 is basically consistent with the structure of the outer valve stent of Embodiment 1 or Embodiment 2; however, in the present embodiment, the outer valve stent 401 is also provided with sets of holes. As shown in FIGS. 28 to 30, the holes 428 are distributed at the structure unit joint 432 of the first structure unit 410 adjacent to the outer valve stent 401 or at the second straight rod 415, meanwhile, a groove structure 430 is provided around the holes 428 to prevent the suture from displacement and falling off. Alternatively, the opening shape of the hole 428 may be a circle, a rounded rectangle, etc.

Figure 27:
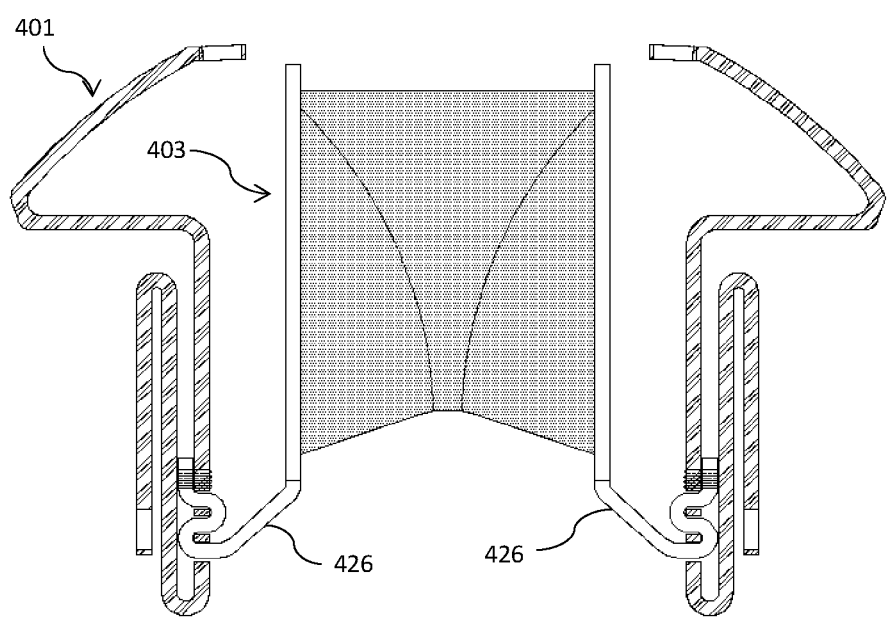
FIG. 27: a structure schematic view of another rigid connection of the assembly manner optional for the outer valve stent and the inner valve stent of the transapical implantable mitral valve device provided by the fourth embodiment of the present invention.

In this embodiment, the filamentous connecting structure 426 passes through each hole of a set of holes 428 on the outer valve stent 401 successively from an end near the left atrium to an end near the left ventricle (FIG. 26) or from an end near the left ventricle to an end near the left atrium (FIG. 27), and the hole 428 is fixed with the filamentous connecting structure 426 passing through the hole with the suture 429, so that the outer valve stent 401 and the inner valve stent 403 are fixed (as shown in FIG. 28 to FIG. 30). The number of holes in each set of holes 428 ranges between 2 and 5, preferably 3. In this embodiment, the number of the sets of holes 428 is the same as the number of the filamentous connecting structures 426, and the number of the filamentous connecting structures 426 ranges between 6 and 15, preferably 9 or 12, which are evenly distributed in the circumferential direction of the inner valve stent 403. The angle G of the lateral wall of the outer valve stent 401 formed by the filament connecting structure 426 and the structure unit 410 of the outer valve stent 401 is between 15 degrees and 75 degrees. There is a certain distance between the outer valve stent 401 and the inner valve stent 403 (i.e. forming a cavity), which can buffer the impact on the inner stent due to compression deformation of the outer stent. Other aspects not specifically described in this embodiment are the same as those in Embodiment 1, such as material of each part of the mitral valve device and provision of skirts.

Embodiment 5

Figure 32:
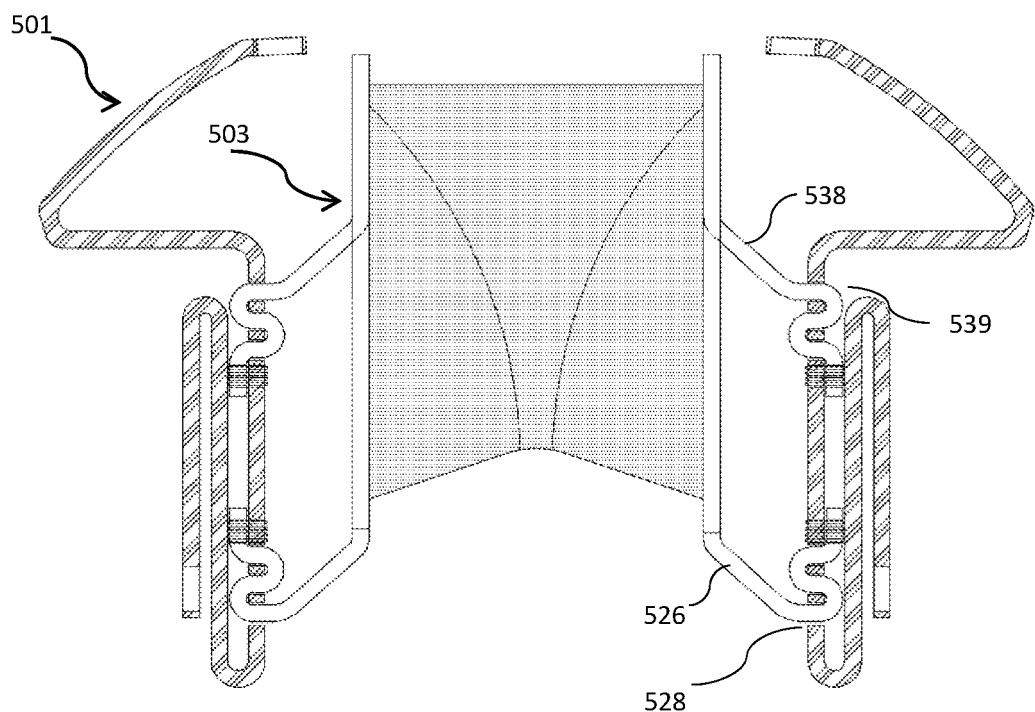
FIG. 32 to FIG. 34: structure schematic views of rigid connection of the assembly manners optional for an outer valve stent and an inner valve stent of a transapical implantable mitral valve device provided by the fifth embodiment of the present invention.
Figure 33:
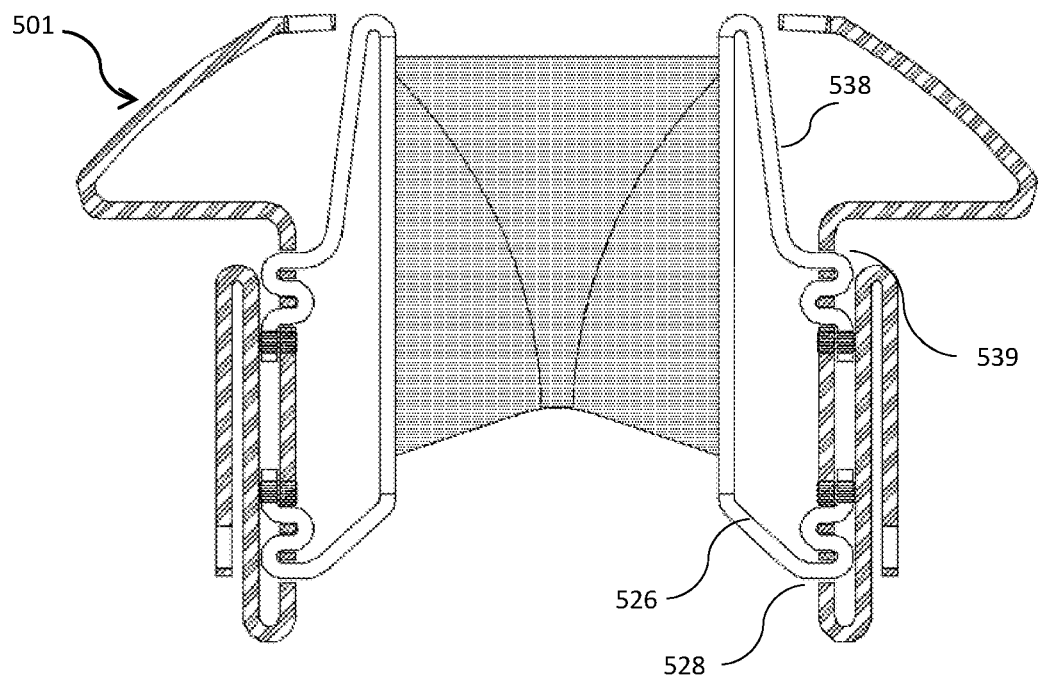

FIG. 32 and FIG. 33 are structure schematic views of rigid connection of the assembly manners optional for the outer valve stent and the inner valve stent of the transapical implantable mitral valve device provided by the fifth embodiment of the present invention. As shown in FIG. 32 and FIG. 33, in this embodiment, the structure of the outer valve stent 501 is basically consistent with that of the outer valve stent in Embodiment 4. The difference lies in that in the present embodiment, a set of holes are arranged on the left atrial end and the left ventricular end on a plurality of or each first structure unit of the outer valve stent 501, as shown in FIG. 32 and FIG. 33, a set of second holes 539 arranged at the end near the left atrium and a set of first holes 528 arranged at the end near the left ventricle, respectively. As in Embodiment 4, in this embodiment, the first holes 528 close to the left ventricular end may be distributed near the left ventricular end of the structure unit joint of the adjacent first structure units of the outer valve stent or at the second straight rod, and the second holes 539 close to the left atrial end may be distributed at the left atrial end of the structure unit joint.

In this embodiment, the structure of the inner valve stent 503 is basically the same as that of the inner valve stent in Embodiment 4; however, in this embodiment, the inner valve stent 503 is provided with filamentous connecting structures at both the left atrial end and the left ventricular end, that is, the second filamentous connecting structure 538 close to the left atrial end and the first filamentous connecting structure 526 close to the left ventricular end. The second filamentous connecting structure 538 may extend from the left atrial end of the inner valve stent 503 (see FIG. 33) or from the middle of the body of the inner valve stent 503 (see FIG. 32) to form.

In this embodiment, the first filamentous connecting structure 526 and the second filamentous connecting structure 538 pass through the first hole 528 and the second hole 539 on the outer valve stent 501 from the end near the atrium to the end near the ventricle or from the end near the ventricle to the end near the atrium, respectively. Furthermore, the filamentous connecting structure passing through each set of holes is fixed with the first structure unit with sutures (such as polymer suture), so that the outer valve stent is fixed with the inner valve stent.

Figure 34:
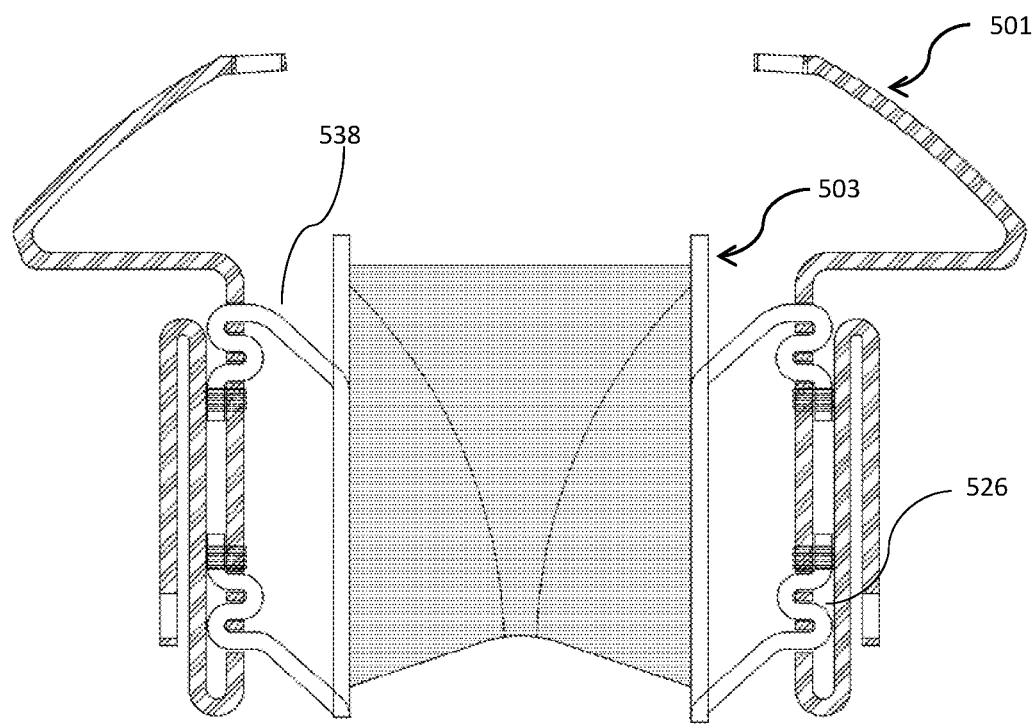

In the present embodiment, the number of holes for each set of second holes 539 or for each set of first holes 528 is between 2 and 5, preferably 3. The number of the filamentous connecting structures 538 at the left atrial end of the inner valve stent 503 ranges between 2 and 5, preferably 3. In order to ensure the stability of the valve, the position of the inner valve stent can be moved within a certain range. The number of the filamentous connecting structures 538 at the left atrial end of the inner valve stent 503 is less than the number of the filamentous connecting structures 526 at the left ventricular end of the inner valve stent 503, wherein the number of the filamentous connecting structures 526 at the left ventricular end is between 6 and 15, preferably 9. The included angles between the first filamentous structure 526 and the second filamentous structure 538 and the side wall of the body formed by the first structure units of the outer valve stent are between 15 degrees and 165 degrees (see FIG. 32 to FIG. 34), so that there is a certain distance (i.e. forming a cavity) between the outer valve stent and the inner valve stent, which can buffer the impact on the inner stent due to compression deformation of the outer stent.

Other aspects not specifically described in this embodiment are the same as those in Embodiment 4, such as materials of various parts of the mitral valve device and provision of skirts, etc.

Embodiment 6

Figure 35:
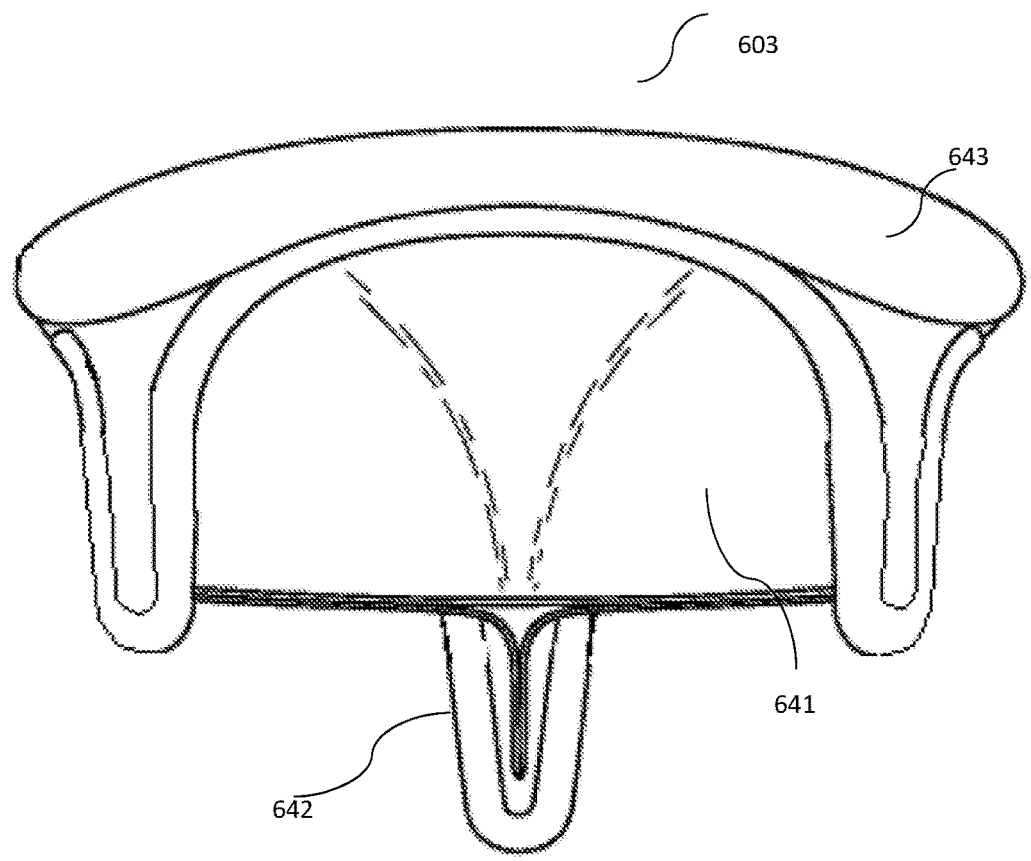
FIG. 35: a structure schematic view of an inner valve stent of a transapical implantable mitral valve device provided by the sixth embodiment of the present invention.

FIG. 35 is a structure schematic view of an inner valve stent of a transapical implantable mitral valve device provided by the sixth embodiment of the present invention, and its appearance is similar to that of a surgical biological prosthetic valve. The surgical biological prosthetic valve has good hemodynamic performance, low incidence of thromboembolism, no need for lifelong anticoagulation after operation, and has long-term durability, but the operation is very difficult and traumatic. In view of this situation, the structure of the surgical biological prosthetic valve is modified so that it can be compressed in a sheath; meanwhile, the modified surgical biological prosthetic valve can be used as the inner valve stent to be fixed with the outer valve stent, and the surgical biological prosthetic valve thus can be fixed on the native diseased mitral valve annulus by intervention, which not only exploits the advantages of the surgical biological prosthetic valve, but also reduces the trauma.

In this embodiment, the inner valve stent 603 includes a frame 642 that is compressible, a valve leaflet structure 641 sewn on the frame 642, and an annular sealing ring 643 for sealing and stabilizing the structure. In this embodiment, the radius of the inner valve stent 603 after radial compression is less than 15 mm, so that the mitral valve device can be loaded into the sheath.

Specifically, the existing surgical valve stent mainly consists of four parts: a valve, a skirt, an annular sealing ring and a metal frame. The annular sealing ring includes an annular sealing ring frame that is made of polymer material and an outer filler; both the metal frame and the annular sealing ring frame are uncompressible. In the present embodiment, the improved surgical biological prosthetic valve as the inner valve stent changes the materials of the metal frame and the annular sealing ring frame into nitinol with hyperelastic properties, meanwhile the shape of the frame is composed of elements with a shape of orthorhombic wave or rhombic shape or the like shape that is compressible.

Figure 36:
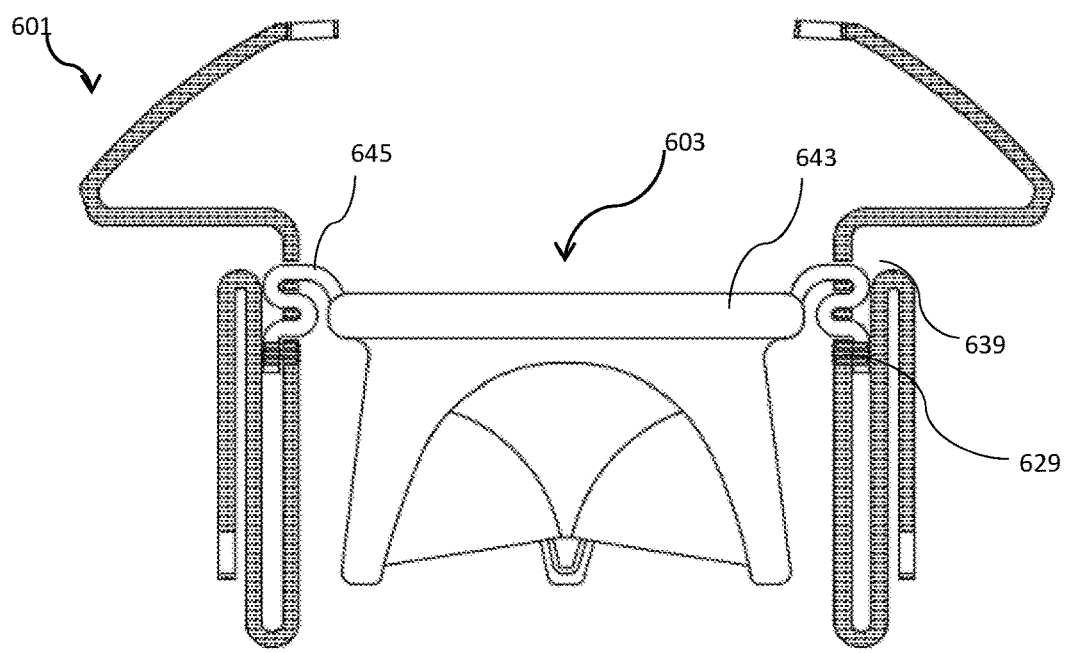
FIG. 36: a schematic view of a connection manner of the inner valve stent and an outer valve stent of the transapical implantable mitral valve device provided by the sixth embodiment of the present invention.

FIG. 36 is a schematic view of a connection manner between the inner valve stent and the outer valve stent of the transapical implantable mitral valve device provided by the sixth embodiment of the present invention. As shown in FIG. 36, in this embodiment, the periphery of the annular sealing ring 643 is provided with filamentous connecting structures 645. In this embodiment, the structure of the outer valve stent 601 is basically the same as that in Embodiment 5, but in this embodiment, the outer valve stent 601 has no first hole at the end near the left ventricular, and sets of second holes 639 are provided only at the end near the left atrial. As shown in FIG. 36, the filamentous connecting structure 645 passes through the second hole 639 of the outer valve stent 601, and the filamentous connecting structure 645 is fixed with the outer valve stent 601 with the suture 629, so that the outer valve stent 601 and the inner valve stent 603 are fixed. Alternatively, the number of second holes 639 in each set is between 2 and 5, preferably 3.

In the present embodiment, the acute angle between the filamentous connecting structure 645 and the axial direction of the mitral valve device ranges from 15 degrees to 75 degrees, so that there is a certain distance between the inner valve stent and the outer stent after connection (i.e., forming a cavity), which can buffer the impact on the inner stent due to the compression deformation of the outer stent.

In the present embodiment, the number of the filamentous connecting structures 645 ranges between 6 and 15, correspondingly, the number of sets of the second holes is between 6 and 15, and the number of the both is the same. In the present embodiment, the shape of the second hole 639 can be a circle, a rounded rectangle and other shapes. In this embodiment, the shape of the filamentous connecting structure 645 may be linear, circular arc, sinusoidal wave or irregular waves.

Like the above embodiments, in the present embodiment, a layer of outer skirt is wrapped on the inner surface and/or outer surface of the outer valve stent 601, and is fixed by suturing, pressing or bonding to avoid peripheral leakage.

Embodiment 7

Figure 37:
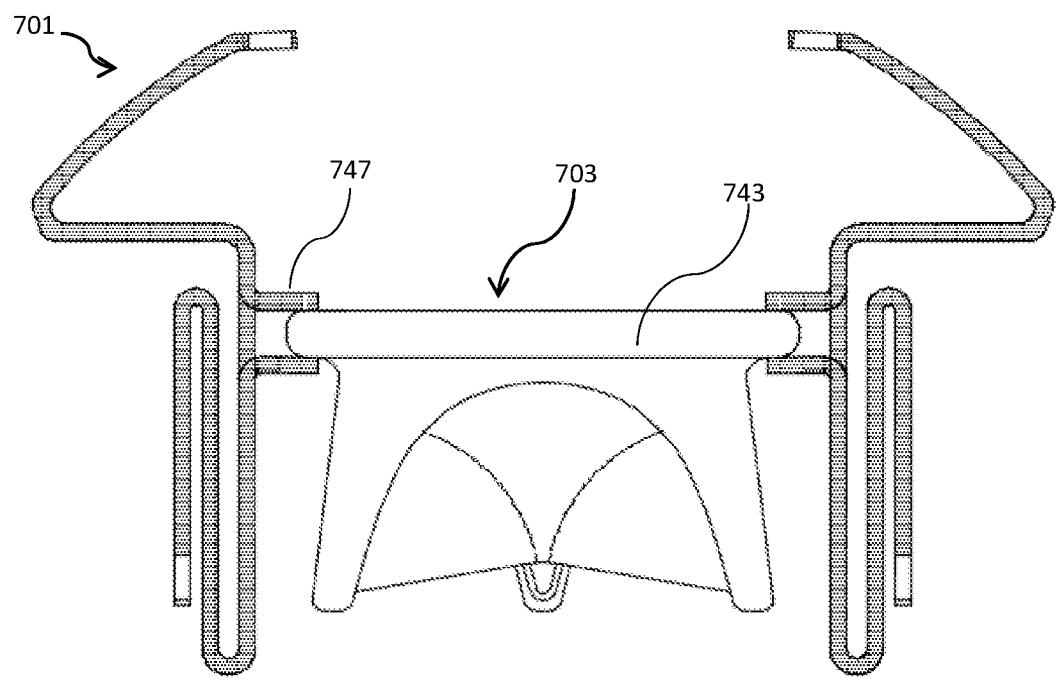
FIG. 37: a schematic view of a connection manner between an inner valve stent and an outer valve stent of a transapical implantable mitral valve device provided by the seventh embodiment of the present invention.

FIG. 37 is a schematic view of a connection manner between the inner valve stent and the outer valve stent of a transapical implantable mitral valve device provided by the seventh embodiment of the present invention. As shown in FIG. 37, in the present embodiment, the structure of the inner valve stent 703 is basically the same as that of Embodiment 6, but there is no filamentous connecting structure. In the present embodiment, the structure of the outer valve stent 701 is basically the same as that of the outer valve stent in Embodiment 1, and a clip structure 747 for clamping the annular sealing ring 743 of the inner valve stent is provided at the end of the first structure unit near the left atrial. In this embodiment, the annular sealing ring 743 of the inner valve stent 703 is clamped on the clip structure 747 of the outer valve stent 701, and the outer valve stent 701 and the inner valve stent 703 are fixed by means of size matching or suture or glue or the like. There is a certain distance between the inner valve stent and the outer stent (i.e. forming a cavity), which can buffer the impact on the inner stent due to compression deformation of the outer stent.

Alternatively, connection of the outer valve stent and the inner valve stent can be fixed by other mechanical connecting structures such as metal wires or metal bayonets, suture, glue or other connection methods. The number of the mechanical connecting structures such as metal wires or metal bayonets ranges between 6 and 15.

As the above embodiments, in the present embodiment, a layer of outer skirt is wrapped on the inner surface and/or outer surface of the outer valve stent 701, and is fixed by suturing, pressing or bonding to avoid peripheral leakage.

When the mitral valve device in each embodiment of the present invention is used, it is loaded on the matched delivery system: the stents are straightened by pulling pull rings at the left ventricular end and left atrial end of the stent, and the mitral valve device is put into the sheath of the delivery system by reducing the outer diameter. With the delivery system, the mitral valve device is implanted into the diseased mitral position of human body through the apex, the outer valve stent of the valve device is anchored at the native mitral valve annulus of human body, and the valve leaflets on the inner valve stent of the valve device open and close under the action of blood dynamics to replace the effect of the native mitral valve.

It can be seen that the transapical implantable mitral valve device provided in the above embodiments connects the outer valve stent with the inner valve stent in different manners, and the design of double layers and incomplete fixation of the inner and outer valve stents makes the outer valve stent and the inner valve stent both relatively fixed and can move independently, so as to ensure that the mitral valve device is not affected by the irregular contour of the diseased mitral valve, the ideal contour is always maintained to ensure functions and avoid leakage of the valve. Moreover, the U-shaped structure unit and S-shaped structure unit arranged in the transapical implantable mitral valve device provided in the above embodiments can be accurately transported to and firmly anchored at the position of the diseased mitral valve. Moreover, the transapical implantable mitral valve device provided in the above embodiments can provide a platform for interventional therapy for the surgical-type mitral valve device.

The description presented in the above exemplary embodiments is only used to illustrate the technical solutions of the present invention, and is not intended to be exhaustive or to limit the present invention to the precise form described. Obviously, it is possible for a person of ordinary skill in the art to make many changes and modifications according to the above teachings. The purpose of selecting and describing the exemplary embodiments is to explain the specific principle and practical application of the present invention, so as to make it easy for other skilled personnel in the art to understand, implement and utilize various exemplary embodiments and various selections and modifications of the present invention. The scope of protection of the present invention is intended to be defined by the appended claims and their equivalents.

What is claimed is:

1. A transapical implantable mitral valve device comprising: an outer valve stent comprising an outer valve stent body, the outer valve stent body comprises a plurality of first structure units arranged in a circumferential direction, and an anchoring unit that is disposed on the outer valve stent body for anchoring the transapical implantable mitral valve device within a human body; at least one of an inner surface and an outer surface of the outer valve stent body being covered with an outer skirt; an inner valve stent disposed inside the outer valve stent and interconnected with the outer valve stent, and a cavity being defined between the outer valve stent and the inner valve stent; and a valve leaflet structure disposed inside the inner valve stent to form a prosthetic valve;

wherein the inner valve stent comprises an inner valve stent body, the inner valve stent body including a plurality of second structure units arranged in the circumferential direction and an axial direction;

wherein the anchoring unit comprises a U-shaped structure unit and a S-shaped structure unit, wherein the S-shaped structure unit is arranged at a left ventricular end of the outer valve stent body; the S-shaped structure unit is formed by bending upwards and then bending downwards to form a folded structure, and the outer side of the S-shaped structure unit is configured to be in contact with an inner side of the mitral valve leaflet for fixing with the mitral valve leaflet;

wherein an opening of the U-shaped structure unit is toward an interior of the mitral valve device;

wherein a lower edge of the U-shaped structural unit is configured to be in contact with an upper side of the mitral valve leaflet;

wherein the U-shaped structure unit is arranged at a left atrial end of the outer valve stent body to locate the transapical implantable mitral valve device at a mitral valve annulus;

wherein the plurality of first structure units are provided with sets of holes, at least one of a left ventricular end of the second structure units, a structure unit joint of the second structure units, and a left atrial end of the second structure units are provided with filamentous connecting structures, each of the filamentous connecting structures penetrates into each hole of the sets of holes and is fixed, so as to connect the outer valve stent with the inner valve stent, and the cavity is defined between the outer valve stent and the inner valve stent; and an angle formed between the filamentous connecting structures and the axial direction of the transapical implantable mitral valve device is 15 degrees to 165 degrees.

2. The transapical implantable mitral valve device of claim 1, wherein at least one of an inner surface and an outer surface of the inner valve stent is covered with an inner skirt.

3. The transapical implantable mitral valve device of claim 1, wherein materials of the outer valve stent and the inner valve stent are hyperelastic alloy or shape memory alloy materials.

4. The transapical implantable mitral valve device of claim 1, wherein tail ends of a plurality of the second structure units at a left ventricular end of the transapical implantable mitral valve device extend and turn out to form a first connecting structure that is connected with the plurality of first structure units of the outer valve stent body so as to connect the outer valve stent with the inner valve stent, and the cavity is defined between the outer valve stent and the inner valve stent;

wherein the first connecting structure forms an out-turning angle of 15 degrees to 165 degrees.

5. The transapical implantable mitral valve device of claim 1, wherein a number of holes for each set of the holes is 2 to 5.

6. The transapical implantable mitral valve device of claim 1, wherein the left ventricular end of the second structure units is provided with filamentous connecting structures, and the structure unit joint or the left atrial end of the second structure units is provided with filamentous connecting structures, a number of filamentous connecting structures at the structure unit joint or the left atrial end is less than a number of filamentous connecting structures at the left ventricular end.

7. The transapical implantable mitral valve device of claim 6, wherein the number of filamentous connecting structures at the left ventricular end is 6 to 15; the number of filamentous connecting structures at the structure unit joint or at the left atrial end is 2 to 5.

8. The transapical implantable mitral valve device of claim 1, wherein the inner valve stent is a surgical biological prosthetic valve, the inner valve stent comprises a frame, the valve leaflet structure arranged inside the frame, and an annular sealing ring arranged at a left atrial end of the frame, wherein the frame and the annular sealing ring are compressible.

9. The transapical implantable mitral valve device of claim 8, wherein the surgical biological prosthetic valve after compression in a radial direction has a radius of less than 15 mm, so that the mitral valve device is loaded into a sheath.

10. The transapical implantable mitral valve device of claim 8, wherein a plurality of filamentous connecting structures are provided at a periphery of the annular sealing ring, and a plurality of sets of holes are provided on the outer valve stent, each of the plurality filamentous connecting structure passes through one set of the plurality of sets of holes and is fixed, so that the outer valve stent is connected with the inner valve stent, and the cavity is defined between the outer valve stent and the inner valve stent;

an acute angle formed by the filamentous connecting structures and an axial direction of the transapical implantable mitral valve device is 15 degrees to 75 degrees.

11. The transapical implantable mitral valve device of claim 8, wherein a clip structure is provided at the end of the plurality of first structure units of the outer valve stent near a left atrial end, the clip structure is used to hold the annular sealing ring, so that the outer valve stent is connected with the inner valve stent, and the cavity is defined between the outer valve stent and the inner valve stent.

12. The transapical implantable mitral valve device of claim 1, wherein a terminal of a left atrial end of the U-shaped structure unit and a terminal of a left ventricular end of the S-shaped structure unit are provided with pull rings, a shape of the pull ring is at least one of circular or rounded rectangle.

13. The transapical implantable mitral valve device of claim 1, wherein a vertical distance between a horizontal plane on which an endpoint of the S-shaped structure unit near the left atrial end is located and a horizontal plane on which an endpoint of the U-shaped structure unit near the left ventricular end is located is 0.5 mm to 4 mm.

14. The transapical implantable mitral valve device of claim 1, wherein the S-shaped structure unit has a thickness on a radial direction of 0.5 mm to 4 mm.

15. The transapical implantable mitral valve device of claim 1, wherein a plurality of the U-shaped structure units constitute a circular structure which has a diameter of 55 mm to 65 mm.

16. The transapical implantable mitral valve device of claim 1, wherein at least one of a number of the first structure units and a number of second structure units is provided to be 6 to 15.

17. The transapical implantable mitral valve device of claim 1, wherein the cavity defined between the outer valve stent and the inner valve stent has a thickness in a radial direction of at least 1.5 mm.

18. The transapical implantable mitral valve device of claim 1, wherein at least one of the outer skirt, an inner skirt and a joint skirt is arranged to seal the transapical implantable mitral valve device, defining an opening at the valve leaflet structure for blood to pass through.

19. The transapical implantable mitral valve device of claim 18, wherein a material of the valve leaflet structure, a material of the outer skirt, a material of the inner skirt, and a material of the joint skirt comprises animal pericardium or polymer material, wherein the animal pericardium comprises bovine pericardium or pig pericardium, the polymer material comprises polytetrafluoroethylene, fiber cloth, or fiber membrane.

* * * * *